United States Patent
Cooke et al.

(10) Patent No.: US 6,642,208 B2
(45) Date of Patent: Nov. 4, 2003

(54) ENHANCEMENT OF VASCULAR FUNCTION BY MODULATION OF ENDOGENOUS NITRIC OXIDE PRODUCTION OR ACTIVITY

(75) Inventors: John P. Cooke, Palo Alto, CA (US); Victor J. Dzau, Newton, MA (US); Gary H. Gibbons, Atlanta, GA (US)

(73) Assignee: The Board of Trustees of the Leland Stanford Junior University, Palo Alto, CA (US)

( * ) Notice: Subject to any disclaimer, the term of this patent is extended or adjusted under 35 U.S.C. 154(b) by 56 days.

(21) Appl. No.: 09/930,833

(22) Filed: Aug. 15, 2001

(65) Prior Publication Data

US 2002/0013288 A1 Jan. 31, 2002

Related U.S. Application Data

(63) Continuation of application No. 09/075,509, filed on May 8, 1998, now Pat. No. 6,337,321, which is a continuation of application No. 08/556,035, filed on Nov. 9, 1995, now Pat. No. 5,891,459, which is a continuation-in-part of application No. 08/336,159, filed on Nov. 8, 1994, now abandoned, which is a continuation-in-part of application No. 08/076,312, filed on Jun. 11, 1993, now Pat. No. 5,428,070.

(51) Int. Cl.[7] .................. A61K 48/00; C12N 15/00; C12N 15/63
(52) U.S. Cl. .................. 514/44; 435/320.1; 435/325
(58) Field of Search .............................. 435/320.1, 325; 514/44

(56) References Cited

FOREIGN PATENT DOCUMENTS

| EP | 0 441 119 A2 | 8/1991 |
|---|---|---|
| EP | 0 546 796 A1 | 6/1993 |
| WO | 93/18156 | 9/1993 |

OTHER PUBLICATIONS

Bai et al., Ann. Thorac. Surg. (1998) vol. 66:814–820.
Cayatte, Antonio J., et al., "Chronic Inhibition of Nitric Oxide Production Accelerates Neointima Formation and Impairs Endothelial Function in Hypercholesterolemic Rabbits," Arteriosclerosis and Thrombosis (May 1994) vol. 14, No. (5):753–759.
Cooke, John P., et al., "Endothelial Dysfunction In Hypercholesterolemia Is Corrected By L–Arginine," Endothelial Mechanisms of Vasomotor Control. Eds, Drexler, Zeiher, Bassenge, and Just; Steinkopff Verlag Darmstadt, (1991) pp:173–181.
Cooke, John P., et al., "Cellular Mechanisms of Atherogenesis and the Effects of Nitric Oxide," Current Opinion in Cardiology (1992) vol. 7:799–804.
Cooke, John P., "Endothelial Dysfunction In Disease States," Current Opinion in Cardiology (1990) vol. 5:637–644.

Cooke, John P., et al., "Antiatherogenic Effects of L–Arginine in the Hypercholesterolemic Rabbit," J. Clin. Invest., The American Society for Clinical Investigation, Inc. (Sep. 1992) vol. 90:1168–1172.
Creager, Mark A., et al., "L–Arginine Improves Endothelium–Dependent Vasodilation in Hypercholesterolemic Humans," J. Clin. Invest., The American Society for Clinical Investigation, Inc. (Oct. 1992) vol. 90:1248–1253.
Drexler, Helmut, et al., "Effect of L–Arginine on Coronary Endothelial Function in Cardiac Transplant Recipients," Circulation (Apr. 1994) vol. 89, No. (4):1615–1623.
Fitzpatrick, David F., et al., "Endothelium–Dependent Vasorelaxing Activity of Wine and Other Grape Products," American Journal of Physiology (Aug. 1993) vol. 265, No. (2):H774–778.
Girerd, Xavier J., et al., "L–Arginine Augements Endothelium–Dependent Vasodilation in Cholesterol–Fed Rabbits," Circulation Research (1990) vol. 67:1301–1308.
Ignarro, Louis J., "Endothelium–Derived Nitric Oxide: Actions And Properties," FASEB Journal (Jan. 1989) vol. 3:31–36.
Janssens, Stefan P., et al., "Cloning And Expression Of A cDNA Encoding Human Endothelium Derived Relaxing Factor/Nitric Oxide Synthase," The Journal Of Biological Chemistry (Jul. 25, 1992) vol. 267, No. (21):14519–14522.
Liu et al., Current Pharmaceutical Design (1996) vol. 2:553–584.
Marín, Jesús, et al., "Role Of Endothelium–Formed Nitric Oxide On Vascular Responses," Gen. Pharmac. (1990) vol. 21, No. (5):575–587.
Marshall et al., Science (1995) vol. 269:1050–1055.
Naruse, Kenshin, et al., "Long–Term Inhibition of NO Synthesis Promotes Atherosclerosis in the Hypercholesterolemic Rabbit Thoracic Aorta," Arteriosclerosis and Thrombosis (May 1994) vol. 14, No. (5):746–752.
Nunokawa, Youichi, et al., "Cloning Of Inducible Nitric Oxide Synthase in Rat Vascular Smooth Muscle Cells," Biochemical and Biophysical Research Communications (Feb. 26, 1993) vol. 191, No. (1):89–94.
Orkin et al., Report and Recommendations of the Panel to Assess the NIH Investment of Research in Gene Therapy.
Palmer, Richard M.J., et al., "Vascular Endothelial Cells Synthesize Nitric Oxide From L–Arginine," Nature (Jun. 1988) vol. 333:664–666.

(List continued on next page.)

Primary Examiner—Anne M. Wehbe'
(74) Attorney, Agent, or Firm—Pamela J. Sherwood; James S. Keddie; Bozicevic, Field & Francis LLP

(57) ABSTRACT

Vascular function and structure is maintained or improved by long term administration of physiologically acceptable compounds which enhance the level of endogenous nitric oxide or other intermediates in the NO induced relaxation pathway in the host. Alternatively, or in combination, other compounds may be administered which provide for short term enhancement of nitric oxide, either directly or by physiological processes.

21 Claims, 14 Drawing Sheets

OTHER PUBLICATIONS

Palmer, Richard M.J., et al., "L–Arginine Is The Physiological Precursor For The Formation Of Nitric Oxide In Endothelium–Dependent Relaxation," Biochemical And Biophysical Communications (Jun. 30, 1988) vol. 153, No. (3):1251–1256.

Rossitch, Eugene Jr., et al., "L–Arginine Normalizes Endothelial Function in Cerebral Vessels from Hypercholesterolemic Rabbits," J. Clin. Invest. The American Society for Clinical Investigation, Inc. (Apr. 1991) vol. 87:1295–1299.

Sawa et al., Circulation (1997) vol. 96 Suppl. II:280–285.

Shears et al., J. Am. Coll. Surg. (1998) vol. 187:295–306.

Tsao, Philip S., et al., "L–Arginine Attenuates Platelet Reactivity in Hypercholesterolemic Rabbits," Arteriosclerosis and Thrombosis (Oct. 1994) vol. 14, No. (10):1529–1533.

Verma et al., Nature (1997) vol. 389:239–242.

Von der Lyden et al., Proc. Natl. Acad. Sci USA (1995) vol. 92:1137–1141.

Von der Leyen, Heiko E., et al., "Gene Therapy Inhibiting Neointimal Vascular Lesion: In Vivo Transfer of Endothelial Cell Nitric Oxide Synthase Gene," Proc. Natl. Acad. Sci. USA (Feb. 1995) vol. 92:1137–1141.

Wallace, Arthur, M.D., Ph. D., "Do Deficiencies Of Endothelial Derived Relaxing Factor Contribute To Myocardial Stunning?," J. Card. Surg. (1993) vol. 8:325–328.

Wang, Bing–Yin, et al., "Dietary Arginine Prevents Atherogenesis in the Coronary Artery of the Hypercholesterolemic Rabbit," JACC (Feb. 1994) vol. 23, No. (2):452–458.

ENHANCEMENT OF VASCULAR FUNCTION BY MODULATION OF ENDOGENOUS NITRIC OXIDE PRODUCTION OR ACTIVITY

This application is a continuation of U.S. Application Ser. No. 09/075,509, filed on May 8, 1998, now U.S. Pat. No. 6,337,321, which is a continuation of U.S. Application Ser. No. 08/556,035, filed on Nov. 9, 1995, now U.S. Pat. No. 5,891,459, which is a continuation in part of U.S. Application Ser. No. 08/336,159, filed on Nov. 8, 1994, now abandoned, which is a continuation in part of U.S. Application Ser. No. 08/076,312, Jul. 11, 1993 now U.S. Pat. No. 5,428,070.

INTRODUCTION

This invention was supported in part by the United States Government under Grant 1KO7HCO2660 (NHLBI). The U.S. Government may have an interest in this application.

TECHNICAL FIELD

The field of this invention is the modulation of NO activity, which finds application in maintaining and improving vascular function and thereby preventing or improving vascular degenerative diseases.

BACKGROUND

Atherosclerosis and vascular thrombosis are a major cause of morbidity and mortality, leading to coronary artery disease, myocardial infarction, and stroke. Atherosclerosis begins with an alteration in the endothelium, which lines the blood vessels. The endothelial alteration results in adherence of monocytes, which penetrate the endothelial lining and take up residence in the subintimal space between the endothelium and the vascular smooth muscle of the blood vessels. The monocytes absorb increasing amounts of cholesterol (largely in the form of oxidized or modified low-density lipoprotein) to form foam cells. Oxidized low-density lipoprotein (LDL) cholesterol alters the endothelium, and the underlying foam cells distort and eventually may even rupture through the endothelium.

Platelets adhere to the area of endothelial disruption and release a number of growth factors, including platelet derived growth factor (PDGF). PDGF, which is also released by foam cells and altered endothelial cells, stimulates migration and proliferation of vascular smooth muscle cells into the lesion. These smooth muscle cells release extracellular, matrix (collagen and elastin) and the lesion continues to expand. Macrophages in the lesion elaborate proteases, and the resulting cell damage creates a necrotic core filled with cellular debris and lipid. The lesion is then referred to as a "complex lesion." Rupture of this lesion can lead to thrombosis and occlusion of the blood vessel. In the case of a coronary artery, rupture of a complex lesion may precipitate a myocardial infarction, whereas in the case of a carotid artery, stroke may ensue.

One of the treatments that cardiologists and other interventionalists employ to reopen a blood vessel which is narrowed by plaque is balloon angioplasty (approximately 300,000 coronary and 100,000 peripheral angioplasties are performed annually). Although balloon angioplasty is successful in a high percentage of the cases in opening the vessel, it unfortunately denudes the endothelium and injures the vessel in the process. This damage causes the migration and proliferation of vascular smooth muscle cells of the blood vessel into the area of injury to form a lesion, known as myointimal hyperplasia or restenosis. This new lesion leads to a recurrence of symptoms within three to six months after the angioplasty in a significant proportion of patients (30–40%).

In atherosclerosis, thrombosis and restenosis there is also a loss of normal vascular function, such that vessels tend to constrict, rather than dilate. The excessive vasoconstriction of the vessel causes further narrowing of the vessel lumen, limiting blood flow. This can cause symptoms such as angina (if a heart artery is involved), or transient cerebral ischemia (i.e. a "small stroke", if a brain vessel is involved). This abnormal vascular function (excessive vasoconstriction or inadequate vasodilation) occurs in other disease states as well. Hypertension (high blood pressure) is caused by excessive vasoconstriction, as well as thickening, of the vessel wall, particularly in the smaller vessels of the circulation. This process may affect the lung vessels as well causing pulmonary (lung) hypertension. Other disorders known to be associated with excessive vasoconstriction, or inadequate vasodilation include transplant atherosclerosis, congestive heart failure, toxemia of pregnancy, Raynaud's phenomenon, Prinzmetal's angina (coronary vasospasm), cerebral vasospasm, hemolytic-uremia and impotence.

Because of their great prevalence and serious consequences, it is critically important to find therapies which can diminish the incidence of atherosclerosis, vascular thrombosis, restenosis, and these other disorders characterized by abnormality of vascular function and structure. Ideally, such therapies would inhibit the pathological vascular processes associated with these disorders, thereby providing prophylaxis, retarding the progression of the degenerative process, and restoring normal vasodilation.

As briefly summarized above, these pathological processes are extremely complex, involving a variety of different cells which undergo changes in their character, composition, and activity, as well as in the nature of the factors which they secrete and the receptors that are up- or down-regulated. A substance released by the endothelium, "endothelium derived relaxing factor" (EDRF), may play an important role in inhibiting these pathologic processes. EDRF is now known to be nitric oxide (NO) or a labile nitroso compound which liberates NO. (For purposes of the subject invention, unless otherwise indicated, nitric oxide (NO) shall intend nitric oxide or the labile nitroso compound which liberates NO.) This substance relaxes vascular smooth muscle, inhibits platelet aggregation, inhibits mitogenesis and proliferation of cultured vascular smooth muscle, and leukocyte adherence. Because NO is the most potent endogenous vasodilator, and because it is largely responsible for exercise-induced vasodilation in the conduit arteries, enhancement of NO synthesis could also improve exercise capacity in normal individuals and those with vascular disease. NO may have other effects, either direct or indirect, on the various cells associated with vascular walls and degenerative diseases of the vessel.

Relevant Literature

Girerd et al. (1990) *Circulation Research* 67:1301–1308 report that intravenous administration of L-arginine potentiates endothelium-dependent relaxation in the hind limb of cholesterol-fed rabbits. The authors conclude that synthesis of EDRF can be increased by L-arginine in hypercholesterolemia. Rossitch et al. (1991) *J. Clin. Invest.* 87:1295–1299 report that in vitro administration of L-arginine to basilar arteries of hypercholesterolemic rabbits reverses the impairment of endothelium-dependent vasodilation and reduces vasoconstriction. They conclude that the abnormal vascular responses in hypercholesterolemic animals is due to a reversible reduction in intracellular arginine availability for metabolism to nitric oxide.

Creager et al. (1992) *J. Clin. Invest.* 90:1248–1253, report that intravenous administration of L-arginine improves endothelium-derived NO-dependent vasodilation in hypercholesterojemic patients.

Cooke et al., "Endothelial Dysfunction in Hypercholesterolemia is Corrected by L-arginine," Endothelial Mechanisms of Vasomotor Control, eds. Drexler, Zeiher, Bassenge, and Just; Steinkopff Verlag Darmstadt, 1991, pp. 173–181, review the results of the earlier references and suggest, "If the result of these investigations may be extrapolated, exogenous administration of L-arginine (i.e., in the form of dietary supplements) might represent a therapeutic adjunct in the treatment and/or prevention of atherosclerosis".

Cooke (1990) *Current Opinion in Cardiology* 5:637–644 discusses the role of the endothelium in the atherosclerosis and restenosis, and the effect that these disorders have on endothelial function.

Cooke (1992) *J. Clin. Invest.* 90:1168–1172, describe the effect of chronic administration of oral L-arginine in hypercholesterolemic animals on atherosclerosis. This is the first demonstration that oral L-arginine supplements can improve the release of NO from the vessel wall. The increase in NO release from the vessel wall was associated with a striking reduction in atherosclerosis in hypercholesterolemic animals. This is the first evidence to support the hypothesis that increasing NO production by the vessel wall inhibits the development of atherosclerosis.

Cooke and Tsao (1992) *Current Opinion in Cardiology* 7:799–804 describe the mechanism of the progression of atherosclerosis and suggest that inhibition of nitric oxide may disturb vascular homeostasis and contribute to atherogenesis.

Cooke and Santosa (1993) In: Steroid Hormones and Dysfunctional Bleeding, AAAS Press, review the activities of EDRF in a variety of roles and suggest that reversibility of endothelial dysfunction may be affected by the stage of atherosclerosis. They conclude that EDRF is a potent vasodilator, plays a key role in modulating conduit and resistance vessel tone, has important effects on cell growth and interactions of circulatory blood cells with a vessel wall, and that disturbances of EDRF activity may initiate or contribute to septic shock, hypertension, vasospasm, toxemia and atherosclerosis.

Fitzpatrick et al., *American Journal of Physiology* 265 (Heart Circ. Physiol. 34):H774–H778, 1993 report that wine and other grape products may have endothelium-dependent vasorelaxing activity in vitro.

Wang et al. (1994) *J. Am. Cell. Cardiol.* 23:452–458, report that oral administration of arginine prevents atherosclerosis in the coronary arteries of hypercholesterolemic rabbits.

Drexler et al. (1994) *Circulation* 89:1615–1623 describe the effect of intravenous arginine upon coronary vascular tone. This was the first evidence that intravenous arginine could restore normal NO-dependent vasodilation in the coronary arteries of patients with cardiac transplants, Tsao et al. (1994) *Circulation* 89:2176–2182 demonstrates that oral administration of arginine to hypercholesterolemic rabbits enhances the release of nitric oxide by the vessel wall, and inhibits monocytes from sticking to the vessel.

Tsao et al. (1994) *J. Arterioscl. Thromb.* 14:1529–1533 reveals that oral arginine administration to hypercholesterolemic rabbits inhibits platelet aggregation (blood clotting). Platelet aggregation plays an important role in causing vascular thrombosis in vascular degenerative disorders.

Von de Leyen et al. (1995) PNAS USA, show that the gene encoding nitric oxide synthase (the enzyme that produces NO) can be inserted into the carotid artery of the rat. This causes the rat carotid artery to make more NO, and thereby enhances vasodilation and inhibits thickening of the vessel wall after balloon angioplasty.

Noruse et al. (1994) *Arterioscler. Thromb.* 14:746–752, report that oral administration of an antagonist of NO production accelerates atherogenesis in hypercholesterolemic rabbits.

Cayette et al. (1994) *Arterioscler. Thromb.* 14:753–759, also report that oral administration of an antagonist of NO production accelerates plaque development in hypercholesterolemic rabbits.

Other references which refer to activities attributed to NO or its precursor include: Pohl and Busse (1989) *Circ. Res.* 65:1798–1803; Radomski et al. (1987) *Br. J. Pharmacol.* 92:181–187; Stamler et al. (1989) *Circ. Res.* 65:789–795; antiplatelet activity); Garg and Hassid (1989) *J. Clin. Invest.* 83:1774–1777; Weidinger et al. (1990) *Circulation* 81:1667–1679; NO activity in relation to vascular smooth muscle growth); Ross (1986) *N. Engl. J. Med.* 314:488–500; Bath et al. (1991) *Arterioscler. Thromb.* 11:254–260; Kubes et al. (1991) *Proc. Natl. Acad. Sci. USA* 89:6348–6352; Lefer et al. (1990) In: Endothelium-Derived Contracting Factors. Basel, S. Karger, pp.190–197; NO activity in relation to leukocyte adhesion and migration); Heistad et al. (1984) *Circ. Res.* 43:711–718; Rossitch et al. (1991) *J. Clin. Invest.* 87:1295–1299; Yamamoto et al. (1988) *ibid* 81:1752–1758; Andrews et al. (1987) *Nature* 327:237–239; Tomita et al. (1990) *Circ. Res.* 66:18–27; Kugiyama et al. (1990) *Nature* 344:160–162; Mitchell et al. (1992) *J. Vasc. Res.* 29:169 (abst.); Minor et al. (1990) *J. Clin. Invest.* 86:2109–2116; NO activity in relation to hypercholesterolemia); Tanner et al. (1991) *Circulation* 83:2012–2020; Kuo et al. (1992) *Circ. Res.* 70:f465–476; Drexler et al. (1991) *Lancet* 338:1546–1550; Schuschke et al. (1994) *Int. J. of Microcircu: Clin. and Exper.* 14(4):204–211; Yao et al. (1992) *Circulation* 86:1302–1309; Higashi et al. (1995) *Hypertension* 25(4 Pt 2):898–902; Kharitonov et al. (1995) *Clin. Sci.* 88(2):135–139; Smulders et al. (1994) *Clin. Sci.* 87(1):37–43; Bode-boger et al. (1994) *Clin. Sci.* 87(3):303–310; Bode-Boger et al. (1994) *Clin. Sci.*; Randall et al. (1994) *Clin. Sci.* 87(1):53–59; Dubois-Rande et al. (1992) *J. Card. Pharm.* 20 Suppl. 12:S211-3; Otsuji et al. (1995) *Am. Heart J.* 129(6): 1094–1100; Nakanishi et al. (1992) *Am. J. of Physio.* 263(6 Pt 2):H1650-8; Kuo et al. (1992) *Circ. Research* 70(3): 465–476; Tanner et al. (1991) *Circulation* 83(6):2012–2020; Meng et al. (1995) *J. Am. Col. Card.* 25(1):269–275; Lefer and Ma (1993) *Arterioscl. and Thromb.* 13(6):771–776; McNamara et al. (1993) *Biochem. and Biophys. Res. Comm.* 193(1):291–296; Tarry and Makhoul (1994) *Arter. and Thromb.* 14(6):983-943; Davies et al. (1994) *Surgery* 116(3):557–568; and Raij (1994) *Kidney Institute* 45:775–781.

SUMMARY OF THE INVENTION

Methods are provided for improving vascular function and structure, particularly modulating vascular relaxation, cellular adhesion, infiltration and proliferation by modulating the level of nitric oxide or active precursor at a physiological site. The methods find use in preventing the degradation of vascular function, particularly as involved with the occurrence of atherosclerosis, restenosis, thrombosis, hypertension, impotence, and other disorders characterized by reduced or inadequate vasodilation. The enhancement of endogenous nitric oxide or secondary messenger availability at a physiological site improves vascular relaxation and thereby relieves symptoms due to inadequate blood flow (such as angina) and can counteract inappropriate elevation of blood pressure. The enhancement of endogenous nitric oxide also inhibits initiation and the progression of atherosclerosis, restenosis, vascular hypertrophy or hyperplasia and thrombosis. This is due to the fact that nitric oxide is not only a potent modulator, but can also inhibit platelets and white blood cells from adhering to the vessel wall. As a prophylaxis or treatment for vascular function deterioration, particularly in atherosclerotic susceptible hosts, the agent is chronically administered at an effective dosage. For restenosis, the agent may be administered for a limited period since this pathological process generally abates 3–6 months after the vascular injury (i.e. angioplasty or atherectomy). Oral administration of L-arginine, precursors to L-arginine, e.g. oligopeptides or polypeptides comprising L-arginine, or proteins comprising high levels of L-arginine, by itself or in combination with L-lysine, particularly further supplemented with GRAS substances which enhance the effectiveness of the active agents, as a dietary supplement will increase NO elaboration and thereby diminish the effects of atherogenesis. Other techniques to enhance NO or secondary messenger availability may be utilized such as increasing the availability of NO synthase, for example, as a result of enhanced expression of NO synthase in the vessel wall, particularly at the lesion site, release of NO from the vessel wall or reduction of degradation of NO or the secondary messenger, cyclic guanosine monophosphate ("cGMP").

DESCRIPTION OF SPECIFIC EMBODIMENTS

Figure 1:
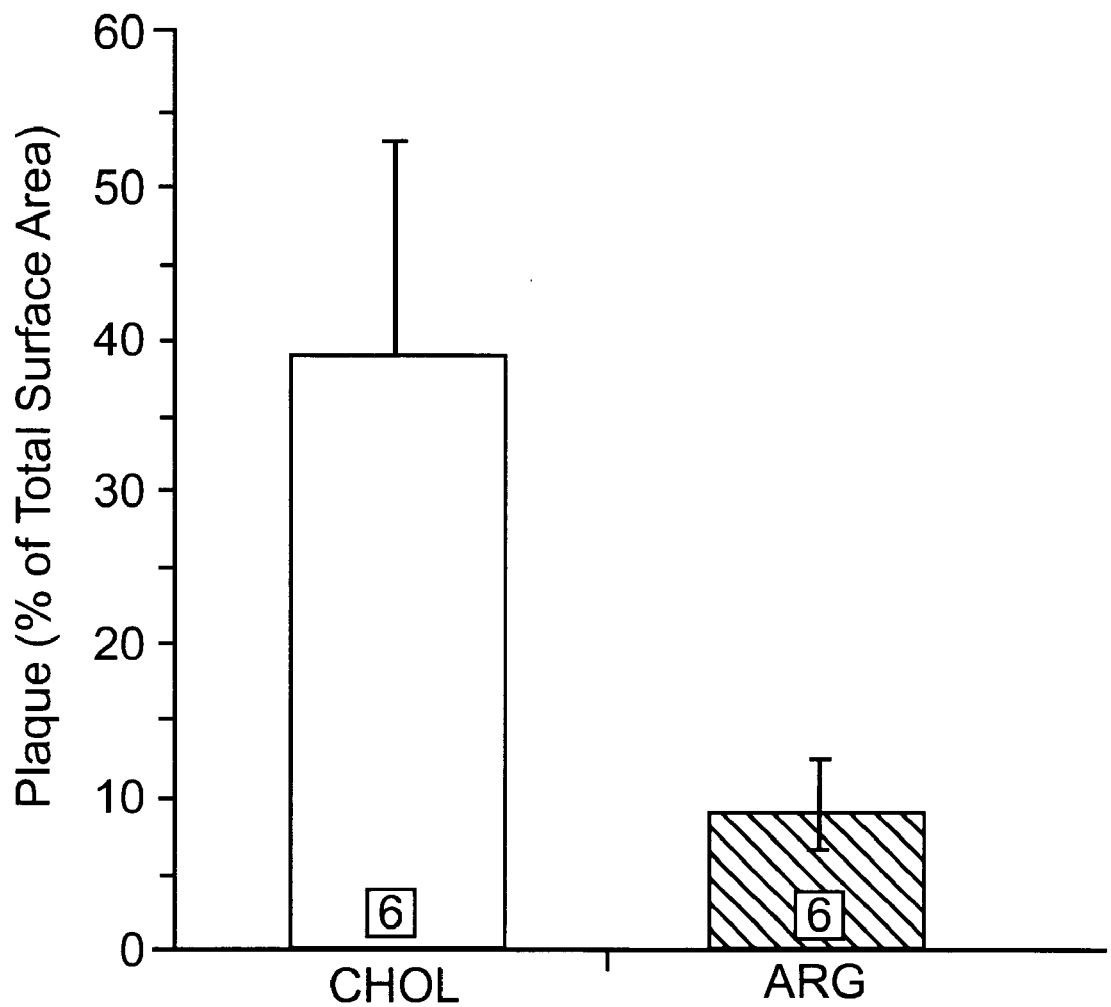
FIG. 1 is a bar diagram of histomorphometric studies of the effect of L-arginine on atherosclerotic plaque in hypercholesterolemic animals. (See Ex. 1)

In accordance with the subject invention, vascular function is maintained or its deterioration inhibited or retarded by enhancing the level or activity of endogenous nitric oxide. By enhancing the level or activity of endogenous nitric oxide, common vascular degenerative diseases such as atherosclerosis, restenosis, hypertension, vasospasm, impotence, angina, and vascular thrombosis, can be treated prophylactically and/or therapeutically. The enhanced level or activity of nitric oxide (which is intended to include any precursor of nitric oxide which results in such enhanced level) can be achieved by modulating the activity, synthesis or concentration of any of the components associated with the formation of nitric oxide in the nitric oxide synthetic pathway, or inhibiting the rate of degradation of nitric oxide, its precursors, or the secondary messengers associated with the relaxation signal. In referring to the enhanced level or activity, the term "effect" will be used to encompass the two situations. The enhanced effect of nitric oxide may be a result of oral or intravenous administration to the patient of a precursor in the metabolic pathway to the production of nitric oxide (such as L-arginine, L-lysine, polypeptides comprising these amino acids, and the like), providing an enzyme in the metabolic pathway to NO, particularly NO synthase, by introduction of the gene for NO synthase under conditions for integration of the gene into the endothelial or other cells and expression of the gene, or by directly adding an enzyme associated with the production of nitric oxide. The enhanced level of nitric oxide may also result from administration of an agent to protect the NO from degradation, such as an oxidant, reductant or superoxide dismutase. Alternatively, the agent may serve to enhance the bioavailability or effectiveness of the primary active agent, such as L-arginine or L-lysine. The agent, individually or in combination, will be administered in a form of other than a natural food source, such as meat or plants as natural protein sources, fruits or products derived therefrom.

One approach is to employ L-arginine and/or L-lysine, as individual amino acids, in combination, or as a precursor to L-arginine, e. g. a monomer or a polypeptide, as a dietary supplement. The amino acid(s) are administered as any physiologically acceptable salt, such as the hydrochloride salt, glutamate salt, etc. They can also be administered as a peptide (e.g., poly-L-arginine, poly-L-lysine, or combinations thereof) so as to increase plasma levels of the NO precursor. Oligopeptides of particular interest include oligopeptides of from 2 to 30, usually 2 to 20, preferably 2 to 10 amino acids, having at least 50 mol % of L-arginine and/or L-lysine, preferably at least about 75 mol % of L-arginine and/or L-lysine, more preferably having at least about 75 mol % of L-arginine and/or L-lysine. The oligopeptides can be modified by being ligated to other compounds, which can enhance absorption from the gut, provide for enhancement of NO synthesis or stability, e.g. reducing agents and antioxidants, and the like.

Naturally occurring sources include protamine or other naturally occurring L-arginine or -lysine containing protein, which is high in one or both of the indicated amino acids, e.g. greater than about 40%, preferably greater than about 50%.

The administration of L-arginine, other convenient NO precursor, or other agent which enhances NO availability, would be in accordance with a predetermined regimen, which would be at least once weekly and over an extended period of time, generally at least one month, more usually at least three months, and as a chronic treatment, could last for one year or more, including the life of the host. The dosage administered will depend upon the frequency of the administration, the blood level desired, other concurrent therapeutic treatments, the severity of the condition, whether the treatment is for prophylaxis or therapy, the age of the patient, the natural level of NO in the patient, and the like. Desirably, the amount of L-arginine and/or L-lysine (R and/or K) or biologically equivalent compound which is used would generally provide a plasma level in the range of about 0.15 to 30 mM. The oral administration of R and/or K can be achieved by providing R and/or K, other NO precursor, or NO enhancing agent as a pill, powder, capsule, liquid solution or dispersion, particularly aqueous, or the like. Various carriers and excipients may find use in formulating the NO precursor, such as lactose, terra alba, sucrose, gelatin, aqueous media, physiologically acceptable oils, e.g. peanut oil, and the like. Usually, if daily, the administration of L-arginine and/or L-lysine for a human host will be about 1 to 12 g per day.

Furthermore, other agents can be added to the oral formulation of the amino acids or polypeptides to enhance their absorption, and/or to enhance the activity of NO synthase, e.g. $B_6$ (50–250 mg/d), folate (0.4–10 mg per daily dose), $B_{12}$ (0.5–1 mg/d) or calcium (250–1000 mg per daily dose). Furthermore, agents known to protect NO from degradation, such as antioxidants (e.g. cysteine or N-acetyl cysteine 200–1000 mg/d Vitamin C (250–2000 mg daily dose), (coenzyme Q 25–90 mg daily dose, glutathione 50–250 mg daily dose), Vitamin E (200–1000 I.U. daily dose), or β-carotene (10–25,000 I.U. daily dose) or other naturally occurring plant antioxidants such as tocopherols, phenolic compounds, thiols, and ubiquinones can be added to the oral or intravenous formulations of R and/or K, or R and/or K-containing peptides. Alternatively, one may include the active agent in a nutritional supplement, where other additives may include vitamins, amino acids, or the like, where the subject active agent will be at least 10 weight %, more usually at least about 25 weight % of the active ingredients.

The administration of R and/or K or its physiologic equivalent in supporting NO can be administered prophylactically to improve vascular function, serving to enhance vasodilation and to inhibit atherogenesis or restenosis, or therapeutically after atherogenesis has been initiated. Thus, for example, a patient who is to undergo balloon angioplasty can have a regimen of R and/or K administered substantially prior to the balloon angioplasty, preferably at least about a week or substantially longer. Alternatively, in a patient, the administration of R and/or K can begin at any time. Conveniently, the amino acid composition can be administered by incorporating the appropriate dose in a prepared food. Types of foods include gelatins, ice creams, cereals, candies, sugar substitutes, soft drinks, and the like. Of particular interest is the incorporation of R and/or K as a supplement in a food, such as a health bar, e.g. granola, other grains, fruit bars, such as a date bar, fig bar, apricot bar, or the like. The amount of R and/or K or the equivalent would be about 1–25 g per dosage or bar, preferably about 2–15 g.

Instead of oral administration, intravascular administration can also be employed, particularly where more rapid enhancement of the nitric oxide level in the vascular system is desired (i.e. as with acute thrombosis of a critical vessel), so that combinations of oral and parenteral administrations can be employed in accordance with the needs of the patient. Furthermore, parenteral administration can allow for the administration of compounds which would not readily be transported across the mucosa from the gastrointestinal tract into the vascular system.

Another approach is to administer the active ingredient of grape skin extract, which is known to enhance NO activity. See Fitzpatrick et al. (1993), supra. The extract can be enriched for the active component by employing separation techniques and assaying the activity of each of the fractions obtained. The grape skin extract can be divided into fractions using a first gel permeation separation to divide the extract by the size of the components. The active fraction(s) can be determined by an appropriate assay, see the experimental section. The active fraction(s) can be further separated using HPLC and an appropriate eluent, conveniently either an isocratic eluent of aqueous acetonitrile or propanol or a linearly varying eluent, using the same solvents. Fractions which are shown to be active and substantially pure, e.g. at least 80 weight %, by thin layer chromatography, mass spectrometry, gas phase chromatography, or the like can then be characterized using infra-red, nuclear magnetic resonance, mass or other spectroscopy.

For oral or intravascular administration, one can provide R and/or K, by itself or in a polypeptide, or its physiological equivalent in supporting NO, together with antioxidants or scavengers of oxygen-derived free radicals (such as sulfhydryl containing compounds) or compounds that prevent the production of oxygen-derived free radicals (such as superoxide dismutase), as it is known that oxygen-derived free radicals (such as superoxide anion) can inactivate nitric oxide. Alternatively, or in addition, one can administer cofactors required for NO synthase activity, such as calcium or folate. The amounts of each of these co-agents can be determined empirically, using the assays in the experimental section to determine NO activity.

The various cofactors that may be used with the NO precursors will vary in amount in relation to the amount of NO precursor and the effectiveness of the cofactor, particularly for oral administration. Generally, the cofactors may be present in amounts that would provide daily doses of folate (0.4–10 mg), $B_6$ (50–250 mg), $B_{12}$ (0.5–1 mg) and/or calcium (250–1000 mg). Usually, where the amount of the NO precursor is greater than about 2 g, it may be administered periodically during the day, being administered 2 to 4 times daily. For the most part, the cofactors will be GRAS substances and will be able to be taken at high dosages without adverse effects on the recipient host.

The subject compositions will be for the most part administered orally and the dosage may take a variety of forms. The dosage may be tablets, pill, capsules, powders, solutions, dispersions, bars, ice creams, gelatins, and the like, formulated with physiologically acceptable carriers, and optionally stabilizers, colorants, flavoring agents, excipients, tabletting additives, and the like. Depending upon the mode of administration, the amount of active agent may be up to about 25 g. For formulations as dietary supplements, individual dosages will generally range from about 0.5 to 5 g, more usually from about 1 to 3 g of the NO precursor.

Alternatively, one can enhance, either in conjunction with the enhancement of precursors to nitric oxides or independently, components of the nitric oxide metabolic pathway. For example, one can enhance the amount of nitric oxide synthase present in the vessel wall, particularly at the site of lesions. This can be done by local administration to the lesion site or systemically into the vascular system. The synthase can be administered using liposomes, slow release particles, or in the form of a depot, e.g. in collagen, hyaluronic acid, biocompatible gels, vascular stents, or other means, which will provide the desired concentration of the NO synthase at the lesion site.

Instead of providing for the enhancement of NO at the physiological site of interest, one can choose to extend the lifetime of the signal transduced as a result of the presence of nitric oxide. Since cGMP is produced intracellularly as a result of a nitric oxide induced signal, employing agents which result in the production of or extending the lifetime of cGMP can be employed. Illustrative agents include cGMP phosphodiesterase inhibitors or agents which increase the amount of guanylate cyclase.

Alternatively, cells can be genetically engineered to provide for constitutive or inducible expression of one or more genes, which will provide for the desired relaxation response, by expressing NO synthase, or other enzyme or protein which is secreted and acts extracellularly. Thus, expression vectors (viral or plasmid) can be prepared which contain the appropriate gene(s) and which can be introduced into host cells which will then produce high concentrations of nitric oxide or other intermediate in the relaxation pathway. These cells can be introduced at the lesion site or at another site in the host, where the expression will induce the appropriate response as to relaxation, proliferation, etc. The NO synthase or cells expressing the NO synthase can be present as depots by encapsulation and positioning at the site of interest. For example, porous stents can be produced which encapsulate the enzyme or cells to protect the enzyme from degradation or being washed away.

Cultured cells can be transfected with expression vectors containing the NO synthase or other gene ex-vivo and then introduced into the vessel wall, using various intra-arterial or intravenous catheter delivery systems. Alternatively, techniques of in vivo gene transfer can be employed to transfect vascular cells within the intact vessel in vivo. The gene(s) can be expressed at high constitutive levels or can be linked to an inducible promoter (which can have tissue specificity) to allow for regulation of expression.

DNA constructs are prepared, where the appropriate gene, e.g. a NO synthase gene, is joined to an appropriate promoter, either with its native termination region or a different termination region, which can provide for enhanced stability of the messenger RNA. Constitutive promoters of particular interest will come from viruses, such as Simian virus, papilloma virus, adenovirus, HIV, Rous sarcoma virus, cytomegalovirus or the like, where the promoters include promoters for early or late genes, or long terminal repeats. Endogenous promoters can include the β-actin promoter, or cell-type specific promoters.

A construct is prepared in accordance with conventional techniques, the various DNA fragments being introduced into an appropriate plasmid or viral vector, normally a vector capable of replication in a bacterial and/or eucaryotic host. Normally, the vector will include a marker, which allows for selection of cells carrying the vector, e.g. antibiotic resistance. The vector will normally also include an origin which is functional in the host for replication. Other functional elements can also be present in the vector.

Once the vector has been prepared and replicated, it can then be used for introduction into host cells. The plasmid vector construct can be further modified by being joined to viral elements which allow for ease of transfection, can provide a marker for selection, e.g. antibiotic resistance, or other functional elements. Introduction of the plasmid vector construct into the host cells can be achieved by calcium phosphate precipitated DNA, transfection, electroporation, fusion, lipofection, viral capsid-mediated transfer, or the like. Alternatively, the expression construct within viral vectors can be introduced by standard infection techniques. For somatic cell gene therapy, autologous cells will generally be employed, although in some instances allogeneic cells or recombinantly modified cells can be employed. Usually the cells employed for genetic modification will be mature endothelial or vascular smooth muscle cells. Occasionally, the cells employed for genetic modification will be progenitor cells, particularly early progenitor cells. For example, myoblasts can be employed for muscle cells or hematopoietic stem cells or high proliferative potential cells can be employed for lymphoid and/or myelomonocytic cells.

Depending upon the nature of the cells, they can be injected -into tissue of the same or different cellular nature, they can be injected into the vascular system, where they may remain as mobile cells or home to a particular site (i.e. the lesion). For the NO synthase gene, the number of cells which are administered will depend upon the nature of the cells, the level of production of the NO synthase, the desired level of NO synthase in the host vascular system, at the lesion site, or the like, whether the enhanced level of NO synthase is the only treatment or is used in conjunction with other components of the nitric oxide synthetic pathway, and the like. Therefore, the particular number of cells to be employed will be determined empirically in accordance with the requirements of the particular patient.

These cells can also be introduced into the circulation by first growing them on the surface of standard vascular graft material (i.e. Dacron or polytetrafluoroethylene grafts) or other synthetic vascular conduits or vascular bioprostheses.

Alternatively, one can use viral vectors, which are capable of infecting cells in vivo, such as adenovirus or retroviruses. In this case, the viral vector containing the NO synthase gene or other gene involved with the relaxation pathway will be administered directly to the site of interest, where it will enter into a number of cells and become integrated into the cell genome. Thus, one can titer the desired level of nitric oxide synthase which is secreted or other protein which is expressed, by providing for one or more administrations of the virus, thus incrementally increasing the amount of synthase which is secreted or other protein which is produced.

Alternatively, one can use modified liposomes as a vehicle for endovascular administration of the vector containing the NO synthase or other gene. One such modified liposome technique involves mixing the liposomes with the vector containing NO synthase. Once the gene expression construct-containing vector is incorporated into the liposome, the liposomes are coated with a protein (e.g. the viral coat protein of the Hemagglutinating Virus of Japan) that increases the affinity of the liposome for the vessel wall.

In some situations, the NO synthase or other gene m the relaxation pathway can be co-transfected with an artificial gene encoding an arginine and/or lysine rich polypeptide susceptible to proteolytic cleavage as an intracellular source of L-arginine and/or L-lysine. In other situations, the NO synthase or other gene can be co-transfected with the superoxide dismutase gene, so as to inhibit the degradation of the nitric oxide.

In some situations, acute treatment may be involved, requiring one or a few administrations. This will normally be associated with compounds which can act as nitric oxide precursors and are other than naturally occurring compounds or are compounds which can be added with naturally occurring compounds to enhance the rate of formation of nitric oxide. Thus, one can provide for acute administration of L-arginine and/or L-lysine and superoxide dismutase to increase the nitric oxide concentration over a restricted period of time. These administrations can be independent of or in conjunction with long term regimens.

The following examples are offered by way of illustration and not by way of limitation.

EXPERIMENTAL

EXAMPLE 1

Anti-atherogenic Effects of Oral Arginine

Study design: (See, Cooke et al., 1992, supra) Male New Zealand white rabbits (n=49) were assigned to one of three treatment groups: 10 were fed with normal rabbit chow for ten weeks (Control); 19 received chow enriched with 1% cholesterol (Chol); and 20 received a 1% cholesterol diet supplemented with 2.25% L-arginine hydrochloride in the drinking water (Arg.). Following ten weeks of the dietary intervention, animals were lightly sedated and the central ear artery cannulated for measurement of intra-arterial blood pressure, followed by collection of blood samples for serum chemistries and plasma arginine. Subsequently the animals were sacrificed and the left main coronary artery and the thoracic aorta were harvested for studies of vascular reactivity and histomorphometry. In some animals, blood was collected for studies of platelet and monocyte reactivity.

Results: Biochemical and physiological measurements. Hypercholesterolemic animals maintained on oral L-arginine supplementation (Arg) experienced a twofold elevation in plasma arginine levels in comparison to animals on a normal (Control) or 1% cholesterol (Chol) diet alone; the elevation in plasma arginine was maintained throughout the come of the study. Serum cholesterol measurements were elevated equally in both groups receiving the 1% cholesterol diet [50±6 vs. 1629±422 vs. 1852±356 mg/dl respectively for Control (=10), Chol (=13), and Arg (=14)]. There were no significant differences in hemodynamic measurements between groups.

Organ chamber studies of isolated vessels: For NO-independent responses, there were no differences between the treatment groups in maximal response or sensitivity to norepinephrine (a vasoconstrictor), or to nitroglycerin (a nitrovasodilator). By contrast, NO-dependent relaxations were attenuated in vessels harvested from hypercholesterolemic animals with a reduction in the maximal response to acetylcholine. In comparison, vessels harvested from hypercholesterolemic animals receiving L-arginine supplementation had improved NO-dependent relaxation to acetylcholine. In a separate study, the effect of chronic arginine supplementation to improve NO-dependent relaxation was confirmed in the hypercholesterolemic rabbit abdominal aorta.

Histomorphometric studies (planimetry of EVG-stained sections): A blinded histomorphometric analysis revealed that medial cross-sectional areas of thoracic aortae were not different between the groups. By contrast, the intimal cross-sectional area (i.e. amount of atherosclerotic plaque) of vessels from hypercholesterolemic animals receiving L-arginine supplementation was reduced in comparison to those from animals receiving cholesterol diet alone. In the Arg animals the reduction in the intimal lesion was most pronounced in the ascending thoracic aorta and left main coronary artery. In the left main coronary artery of hypercholesterolemic animals receiving arginine, essentially no atherosclerotic plaque developed.

Changes in lesion surface area: In a second series of studies, the extent of the thoracic aorta involved by lesions was examined. In hypercholesterolemic rabbits receiving vehicle (n=6) or L-arginine supplement (n=6), thoracic aortae (from left subclavian artery to diaphragm) were harvested after ten weeks of treatment, bisected longitudinally, and stained with oil-red O. Vessels were photographed and vessel and lesion surface area determined by planimetry. Approximately 40% of the total surface area was covered with plaque in thoracic aortae from hypercholesterolemic animals receiving vehicle, whereas in thoracic aortae from arginine-treated hypercholesterolemic animals, less than 10% of the surface area was covered with plaque (FIG. 1).

To summarize, dietary arginine supplementation increases plasma arginine levels, but does not alter serum cholesterol. This is associated with significant improvement in NO-dependent vasodilation as judged by bioassay. Finally, the improvement in NO-dependent vasodilation is associated with reduction in thickness and area of the lesions in vessels from hypercholesterolemic animals.

EXAMPLE 2

Inhibition of Platelet Aggregation by Oral L-arginine

Figure 2:
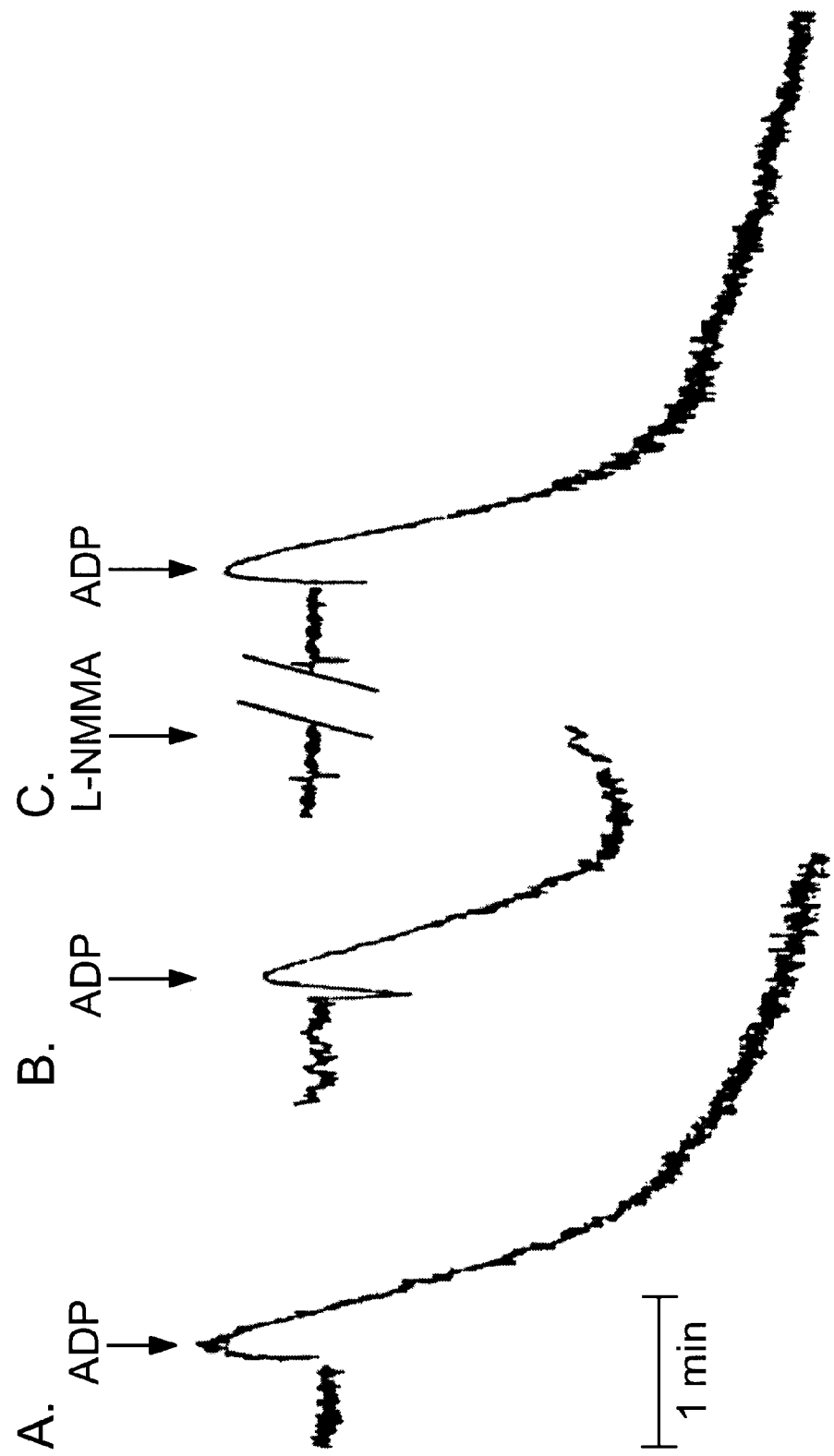
FIG. 2 is a nephelometric scan of the effect of L-arginine diet supplement on platelet reactivity as evidenced by platelet aggregation initiated by adenosine diphosphate. (See Ex. 2) A) aggregation of platelets from hypercholesterolemic rabbit; B) reduced aggregation of platelets from hypercholesterolemic rabbit treated with L-arginine; C) antagonism of NO synthase by LNMMA reverses the beneficial effect of L-arginine.

The effect of L-arginine supplementation on platelet reactivity in rabbits that had normal chow (Control; n=6), a 1% cholesterol diet (Chol; n=5), or a 1% cholesterol diet supplemented with oral arginine (Arg; n=6), as detailed above, was examined. Arterial blood obtained after central ear artery cannulation was anticoagulated with 13 mM sodium citrate. Platelet-rich suspension was prepared by washing platelets in calcium-free Krebs-Henseleit solution and resuspending them in Tyrode's solution with albumin. Aggregation was initiated by addition of adenosine diphosphate and monitored by standard nephelometric techniques. In platelets derived from Chol animals, aggregation was not different in rate or maximum extent in comparison to platelets from Control animals (A, in FIG. 2). By contrast, aggregation of platelets from Arg animals was reduced by 50% (B, in FIG. 2).

This reduction in platelet aggregation was associated with a two-fold greater cGMP content in aggregated platelets from arginine-treated animals. The reduction of platelet reactivity could be reversed by administration of N-methylarginine ($10^{-4}$ M) in vitro (C, in FIG. 2). Therefore, the anti-platelet effect of chronic oral arginine administration can be credited to an increased synthesis of endogenous NO. Furthermore, NO synthesis may be induced in both the platelets and the endothelium.

EXAMPLE 3

Inhibition of Monocyte Adherence

A. Functional Binding Assay: To determine if oral arginine supplementation affects monocyte adherence, blood was collected from rabbits fed normal chow (=6) a 1% cholesterol diet (=6), or a 1% cholesterol diet supplemented with L-arginine (=6), as described above. Mononuclear cells were purified from blood by Ficoll-paque density gradient centrifugation. In these preliminary studies, adhesion was examined of blood leukocytes to a transformed endothelial cell line, bEnd3 (mouse brain-derived polyoma middle T antigen transformed endothelial cells). The Bend3 cells display the morphology of endothelial cells, and like human endothelial cells are capable of uptake of acetylated low-density lipoprotein and express adhesion molecules in a cytokine-regulatable fashion. Cultured cells were grown to confluence in 0.5 $cm^2$ Lab-Tek chamber slides (MilesScientific) and treated with control medium or with LPS (1 mg/ml) or TNFα (25 U/ml) for 18 hours. Cultures were washed with fresh assay buffer, and low, medium, or high concentrations of leukocytes (0.75, 1.5, or $3 \times 10^5$ cells/ml, respectively) were added per well. Following a 30-minute incubation on a rocking platform at room temperature to allow binding, the slides were inverted and immersed in buffer containing 2% (v/v) glutaraldehyde, such that non-adherent cells were lost and adherent cells were fixed to the monolayer. The adherent mononuclear cells were enumerated using video-light microscopy.

Monocytes from hypercholesterolemic animals (Chol) exhibited greater adherence, consistent with observation by others, that monocytes from hypercholesterolemic cats or humans exhibit greater adherence to cultured endothelial cells. (deGruijter et al. (1991) *Metabol. Clin. Exp.* 40:1119–1121; Fan et al. (1991) *Virchows Arch. B Cell Pathol.* 61:19–27).

In comparison to monocytes derived from vehicle-treated hypercholesterolemic animals (Chol), those from arginine-treated hypercholesterolemic animals (Arg) were much less adherent. This data shows that the arginine treatment inhibits adhesion of monocytes to the endothelium, which is the first observable event in atherogenesis.

EXAMPLE 4

Dietary L-Arginine Inhibits the Enhanced Endothelial-Monocyte Interaction In Hypercholesterolemia The earliest observable abnormality of the vessel wall in hypercholesterolemic animals is enhanced monocyte adherence to the endothelium, which occurs within one week of a high cholesterol diet. This event is thought to be mediated by the surface expression of endothelial adhesion molecules and chemotactic proteins induced by hypercholesterolemia.

Another endothelial alteration that occurs in parallel is a reduced activity of nitric oxide (i.e., NO), derived from metabolism of L-arginine. As shown above chronic dietary supplementation with L-arginine restores NO-dependent vasodilatation in hypercholesterolemic rabbits, and that this improvement in NO activity is associated with a striking anti-atherogenic effect. In the following study was tested the hypothesis that the anti-atherogenic effect of dietary arginine was mediated by endothelial derived NO which inhibits monocyte-endothelial cell interaction.

Methods. Animals. Male New Zealand White rabbits were pair fed, receiving one of the following dietary interventions for two weeks: normal rabbit chow (Cont, n=7); rabbit chow enriched with 1% cholesterol (Chol, n=7); or 1% cholesterol chow supplemented with 2.25% L-arginine HCl in the drinking water (Arg, n=7) ad libitum throughout the course of the study. In a second series of studies designed to further explore the role of endogenous NO on monocyte-endothelial cell interaction, another group of animals were pair fed, receiving a normal rabbit diet supplemented with either vehicle control (N=5) or the NO synthase antagonist, nitro-L-arginine (L-NA, 10 mg/100 ml; n=5), administered in the drinking water ad libitum throughout the course of the study (for an average daily dose of 13.5 mg/kg/day). In a third series of experiments animals received a normal diet and either vehicle (n=4), L-NA (13.5 mg/kg/day; n=4), or L-NA and hydralazine (n=4) added to the drinking water for two weeks. At this dose, hydralazine (5 mg/kg/day) reversed the increase in blood pressure induced by L-NA. One day before sacrifice (after 2 weeks of dietary intervention), animals were lightly sedated and the central ear artery was cannulated for collection of blood samples.

Mononuclear cell culture and isolation. Murine monocytoid cells, WEHI 78/24 cells were grown in Dulbecco's Modified Eagle's Medium supplemented 10% fetal calf serum (vol/vol) and were kept in an atmosphere of 5% $CO_2$/95% air. Prior to binding studies, mononuclear cells were fluorescently labeled with TRITC (3 $\mu$g/ml). To confirm the results using WEHI cells, in some studies binding studies were performed in parallel using rabbit mononuclear cells. Mononuclear cells were isolated from fresh whole blood of Control rabbits before sacrifice.

Preparation of aortic endothelium and binding assay. After 2 weeks of the dietary intervention, the thoracic aortae were removed and placed in cold, oxygenated saline. A 15 mm segment of thoracic aorta was excised from a point immediately distal to the left subclavian artery to the midthoracic aorta. The segments were then carefully opened longitudinally and placed into culture dishes containing HBSS medium. Aortic strips were fixed to the culture dish using 25 gauge needles so as to expose the endothelial surface to the medium. Culture dishes were then placed on a rocking platform at room temperature.

After 10 minutes the HBSS medium was replaced by binding medium containing WEHI cells. The aortic strips were incubated with the mononuclear cells for 30 minutes. The medium was then replaced by fresh binding medium without cells to remove non-adherent cells. The aortic segments were then removed and placed on a glass slide, and adherent cells counted under epifluorescent microscopy from at least 30 sites on each segment.

Figure 3:
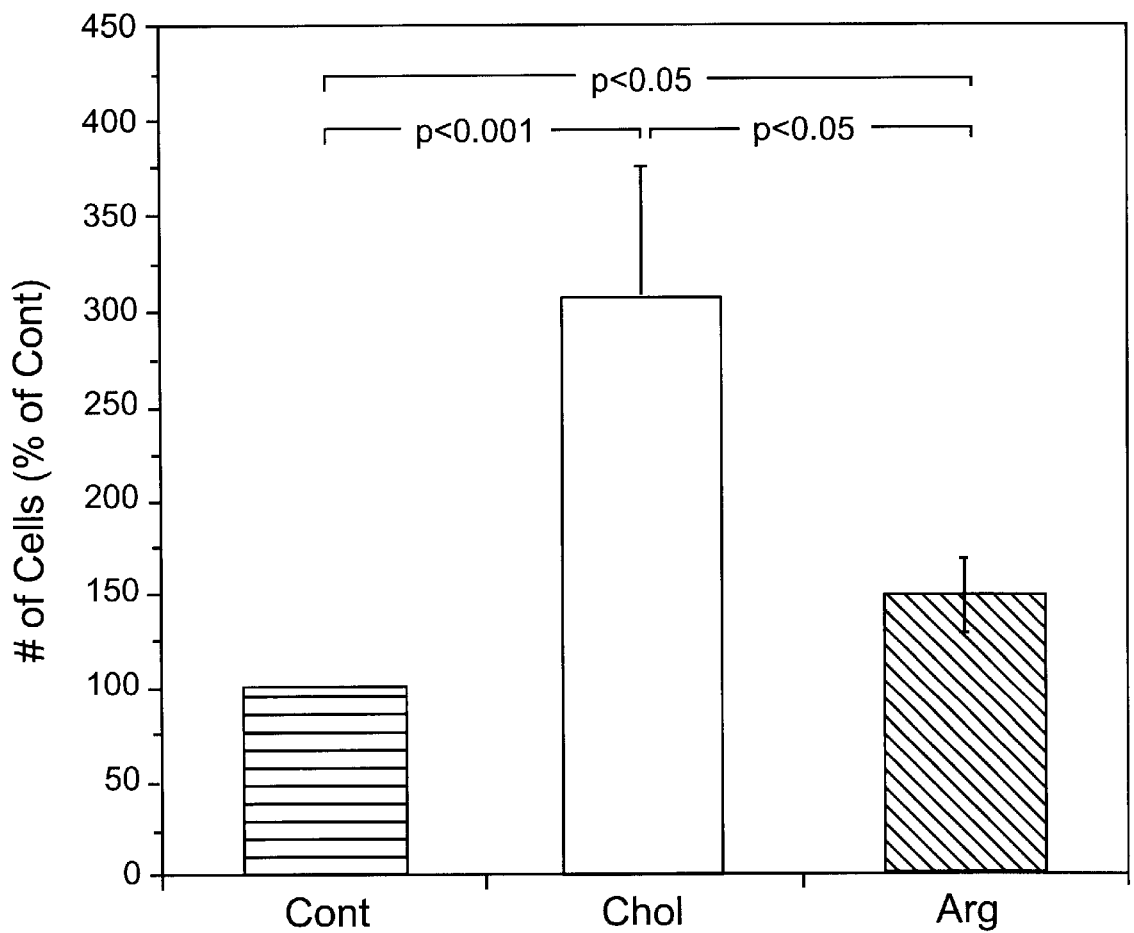
FIG. 3 is a bar diagram comparing the effect of L-arginine diet supplement on cell binding to aortic endothelium of hypercholesterolemic animals. (See Ex. 4)

Results. Monocyte adhesion to rabbit aortic endothelium. Exposure of WEHI 78/24 cells to normal rabbit aortic endothelium results in a minimal cell binding in this ex vivo adhesion assay. However, when WEHI cells were incubated with aortic endothelium from hypercholesterolemic animals (Chol; n=7), cell binding was enhanced 3-fold in comparison to Cont (n=7). The increased cell binding manifested by aortic endothelium of hypercholesterolemic animals was significantly attenuated by L-arginine supplementation (n=7). (FIG. 3) Similar results were achieved when adhesion assays were performed in parallel with mononuclear cells that were freshly isolated from Cont animals (n=2) in each of the three groups.

Effect of chronic NO synthase inhibition on endothelial adhesiveness. To further investigate the role of endothelium-derived NO in modulating endothelialmonocyte interaction, an additional series of binding studies were performed using thoracic aorta from animals that received regular chow supplemented with vehicle (n=5) or the NO synthase inhibitor, L-NA (n=5). The adhesion of WEHI cells was markedly increased when incubated with aortic endothelium from L-NA animals compared to control endothelium. This effect could not be attributed to hypertension caused by L-NA since concomitant administration of hydralazine normalized blood pressure but did not reverse the augmentation of cell binding induced by L-NA.

In a separate series of studies it was confirmed that chronic administration of L-NA (the inhibitor of NO synthase) significantly inhibited generation and release of NO from the vessel wall (as measured by chemiluminescence), compared to vessels from animals treated with vehicle or arginine.

The salient findings of this investigation are: 1) monocyte binding to the endothelium ex vivo is increased in vessels from hypercholesterolemic animals; 2) this increase in monocyte binding is attenuated in hypercholesterolemic animals treated chronically with the NO precursor L-arginine; 3) monocyte binding to the endothelium is increased in vessels from normocholesterolemic animals treated with the NO synthase antagonist L-nitro-arginine; and 4) this effect of NO synthase antagonism was not reversed by administration of hydralazine in doses sufficient to normalize blood pressure. These findings are consistent with the hypothesis that NO inhibits monocyte-endothelial cell interaction.

To conclude, an ex vivo model of monocyte binding has been used to study the increase in endothelial adhesiveness induced by hypercholesterolemia. Endothelial adhesiveness is attenuated by oral administration of the NO precursor L-arginine is shown. Conversely, inhibition of NO synthase activity by oral administration of nitro-arginine strikingly increases endothelial affinity for monocytes ex vivo. The data are consistent with NO being an endogenous antiatherogenic molecule.

EXAMPLE 5

Figure 4:
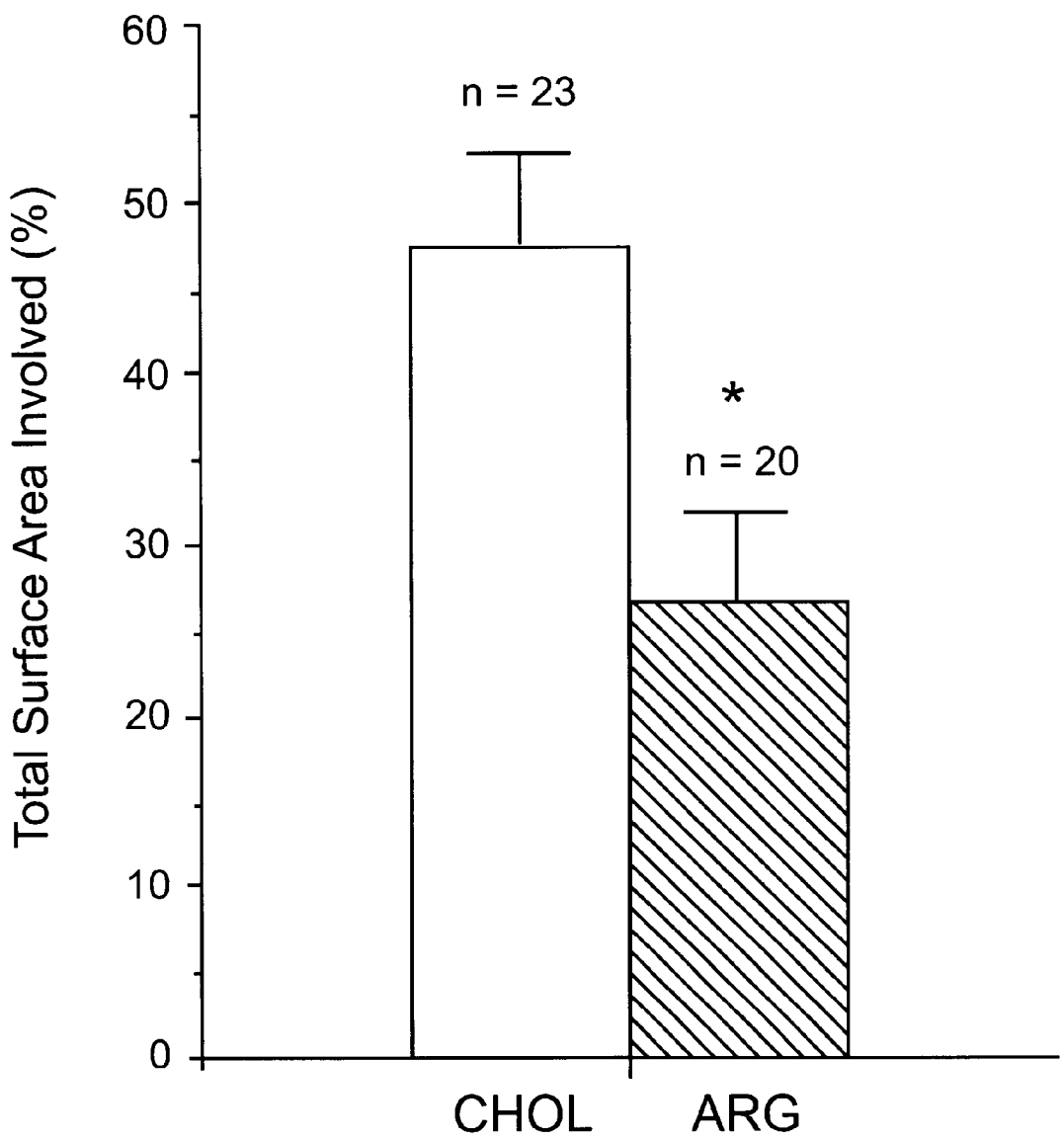
FIG. 4. Lesion surface area of thoracic aortae from all arginine treated hypercholesterolemic animals (ARG, weeks 14–23) is reduced in comparison to that of hypercholesterolemic animals receiving vehicle (CHOL, weeks 14–23). (See Ex. 5)

Oral Arginine Causes Regression of Atherosclerosis in Hypercholesterolemic Rabbits Our previous work demonstrated that oral arginine could prevent the development of plaque in hypercholesterolemic animals but it was not known if preexisting plaque could be affected by arginine treatment. This is clinically important if arginine is to be useful in the treatment of pre-existing atherosclerosis in humans. Accordingly, New Zealand white rabbits (n=85) received normal chow or 0.5% cholesterol chow for 10 weeks. Subsequently, half of the hypercholesterolemic rabbits were given 2.25% (W/V) L-arginine in their drinking water. Thoracic aortae were harvested at weeks 10, 14, 18, or 23. Rings of aorta were used to assess NO-dependent vasodilation to acetylcholine (ACh). Maximal relaxation to ACh in the hypercholesterolemic rabbits receiving vehicle (CHOL) became progressively attenuated from 53.4% (at week 10) to 17.4% (by week 23). Planimetry of the luminal surface of the aortae from CHOL animals revealed a progressive increase in plaque area from 30.3% (at week 10) to 56.5% (by week 23) of the total surface of the thoracic aorta. By contrast, hypercholesterolemic animals receiving arginine (ARG) manifested improved endothelium-dependent relaxation associated with a reduction of plaque area at 14 and 18 weeks. Lesion surface area in all arginine treated hypercholesterolemic animals (weeks 14–23) was significantly reduced in comparison to vehicle-treated hypercholesterolemic animals (FIG. 4). The arginine-induced improvement in endothelium-dependent relaxation was associated with an increased generation of vascular NO, and a reduced generation of vascular superoxide anion. By 23 weeks, 3 of 7 ARG animals had persistent improvement in NO-dependent vasodilation and exhibited a further reduction of plaque area to 5.4%

Conclusions: hypercholesterolemia induces a progressive loss of NO-dependent vasodilation associated with progressive intimal lesion formation. Administration of L-arginine to animals with pre-existing intimal lesions augments vascular NO elaboration, reduces superoxide anion generation, and is associated with a reduction in plaque area. This is the first demonstration that restoration of NO activity can induce regression of preexisting intimal lesions, and provides evidence that L-arginine therapy may be of potential clinical benefit.

EXAMPLE 6

Oral Arginine Administration Restores Vascular NO Activity and Inhibits Myointirnal Hyperplasia after Balloon Injury in Hypercholesterolemic Rabbits.

Purpose. The purpose of this study was to determine if the alterations in vascular function and structure following balloon angioplasty in hypercholesterolemic rabbits could be inhibited by restoration of endogenous nitric oxide (NO) activity.

Methods. Twenty-eight New Zealand white rabbits were randomized into one of three dietary groups and received either normal rabbit chow, 0:5% cholesterol diet, or 0.5% cholesterol-diet plus L-arginine hydrochloride (2.25% W/V) in the drinking water. After six weeks of dietary intervention, cleft iliac artery of each animal was subjected to a balloon angioplasty. Four weeks later, the iliac arteries were harvested for vascular reactivity studies and immunohistochemistry.

Figure 5:
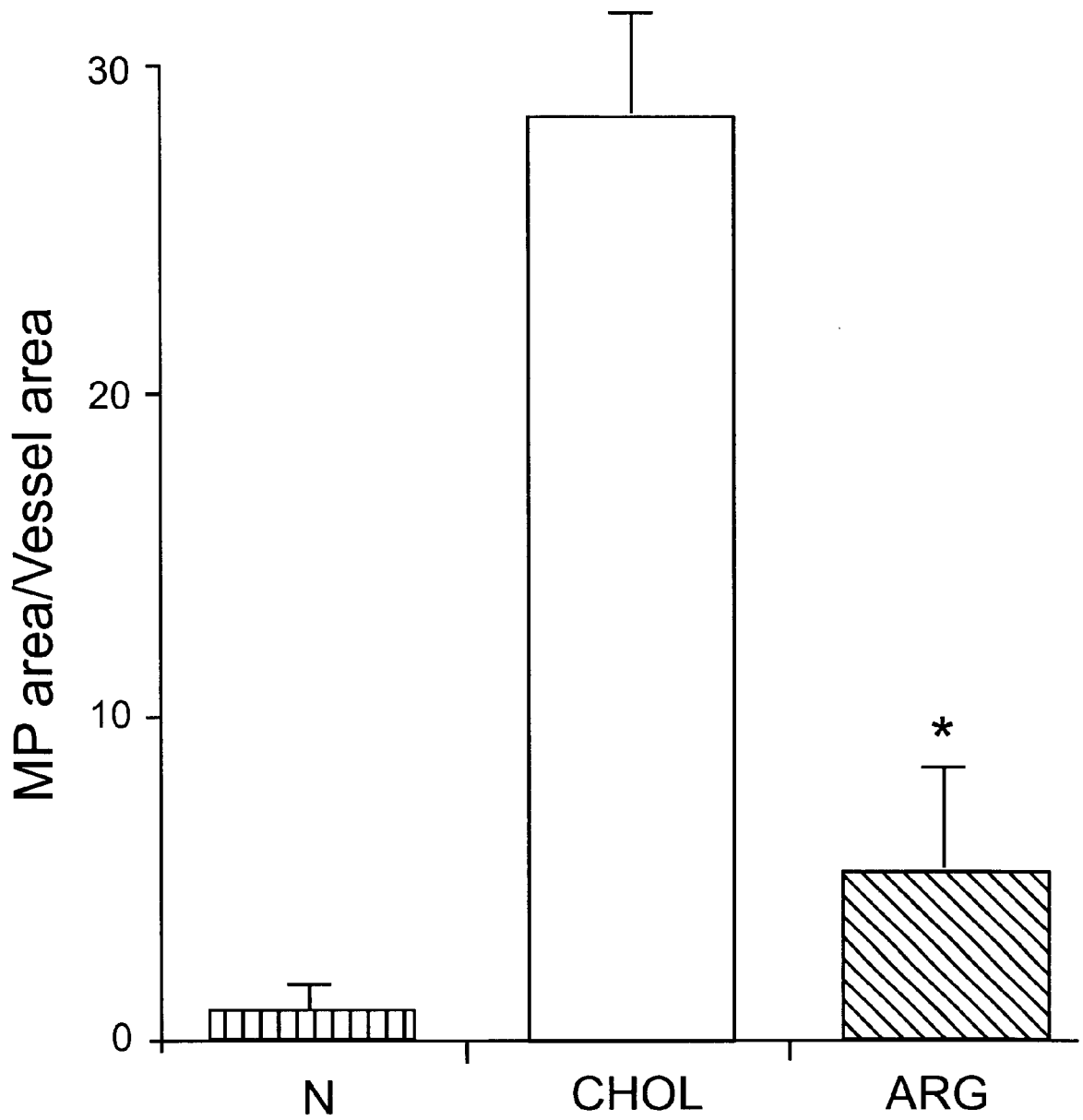
FIG. 5. Macrophage accumulation in iliac arteries 4 weeks following balloon injury. (Macrophage infiltration into the vessel wall initiates and accelerates plaque formation). Data is expressed as a percent of the vessel that contain macrophages. Balloon injury in hypercholesterolemic rabbits (CHOL) results in a marked increase in arterial macrophage accumulation compared with injured iliac arteries from rabbits on normal chow (CONT). Macrophage accumulation in iliac arteries from hypercholesterolemic rabbits receiving L-arginine (ARG) is significantly reduced compared to the CHOL group. (*; $p<0.01$, ARG v. CHOL). This study revealed that oral arginine treatment markedly reduced the infiltration of monocytes/macrophages into the vessel wall, explaining in part the effect of arginine to inhibit plaque formation. (See Ex. 6)

Results. The bioassay studies indicated that endothelium-derived NO activity was inhibited in hypercholesterolemic animals in comparison to normocholesterolemic animals. The administration of arginine partially restored endothelium-derived NO activity. Balloon angioplasty induced intimal thickening which was largely composed of vascular smooth muscle cells and extracellular matrix. In the setting of hypercholesterolemia, vascular injury induced an exuberant myointimal lesion that was augmented by the accumulation of lipid-laden macrophages. Administration of L-arginine induced a quantitative as well as qualitative change in the lesion. Dietary arginine reduced intimal thickening in the injured vessels of hypercholesterolemic animals, and substantially inhibited the accumulation of macrophages in the lesion (FIG. 5).

Conclusions. We report that the lesions induced by balloon angioplasty in hypercholesterolemic animals are markedly reduced by oral administration of arginine. Moreover, we find that the nature of the lesion is altered, with a striking reduction in the percentage of macrophages comprising the lesion. Hypercholesterolemia induces an endothelial vasodilator dysfunction in the rabbit iliac artery that is reversible by chronic oral administration of arginine.

EXAMPLE 7

Nitric Oxide Regulates Monocyte Chemotactic Protein-1

Our previous studies had established that oral arginine administration could enhance vascular NO synthesis. This increase in vascular NO synthesis was associated with inhibition of monocyte adherence and accumulation in the vessel wall (thereby reducing the progression, and even inducing regression, of plaque). The question remained: "How does vascular nitric oxide inhibit monocyte adherence and accumulation in the vessel wall?"

Monocyte chemotactic protein-1 (MCP-1) is a 76-amino acid chemokine thought to be the major chemotactic factor for monocytes (chemotactic factors are proteins that attract white blood cells). We hypothesized that the anti-atherogenic effect of NO may be due in part to its inhibition of MCP-1 expression.

Methods and Results. Smooth muscle cells (SMC) were isolated from normal rabbit aortae by explant method. Cells were then exposed to oxidized LDL (30 $\mu$g/ml) (which is known to induce vascular cells to synthesize MCP-1). The expression of MCP-1 in SMC was associated with an increased generation of superoxide anion by the SMC, and increased activity of the transcriptional protein NFκB. All of these effects of oxidized LDL cholesterol were reduced by previous exposure of the SMC to the NO-donor DETA-NONOate (100 $\mu$M) (p<0.05). To determine if NO exerted its effect at a transcriptional level, SMC and COS cells were transfected with a 400 bp fragment of the MCP-1 promoter. Enhanced promoter activity by oxLDL was inhibited by DETA-NO.

To investigate the role of endogenous NO in the regulation of MCP-1 in vivo, NZW rabbits were fed normal chow, normal chow plus nitro-L-arginine (L-NA) (to inhibit vascular NO synthesis), high cholesterol diet (Chol), or high cholesterol diet supplemented with L-arginine (Arg) (to enhance NO synthesis). After two weeks, thoracic aortae were harvested and total RNA was isolated. Northern analysis demonstrated increased expression of MCP-1 in Chol and L-NA aortae; this expression was decreased in aortae from Arg animals. These studies indicate that the anti-atherogenic effect of NO may be mediated in part by its inhibition of MCP-1 expression. NO inhibits the generation of superoxide anion by the vascular cells and thereby turns off an oxidant-responsive transcriptional pathway (i.e. NFκB-mediated transcription) activating MCP-1 expression.

EXAMPLE 8

Nitric Oxide Inhibits the Expression of an Endothelial Adhesion Molecule Known to be Involved in Atherosclerosis Vascular cell adhesion molecule (VCAM-1) is an endothelial adhesion molecule that binds monocytes. This molecule is expressed by the endothelium of hypercholesterolemic animals, and is expressed by endothelial cells overlying plaque in animals and humans. This adhesion molecule is believed to participate in monocyte adherence and accumulation in the vessel wall during the development of plaque. Other workers have shown that the expression of this molecule is regulated by an oxidant-responsive transcriptional pathway mediated by the transcriptional factor NFκB. Endothelial cells exposed to oxidized LDL cholesterol (or cytokines like TNF-α) begin to generate superoxide anion. Superoxide anion turns on oxidant-responsive transcription leading to the expression of VCAM-1 and MCP-1 (and probably other genes that participate in atherosclerosis). Our data indicates that NO inhibits the generation of superoxide anion, thereby turning off these oxidant-responsive transcriptional pathways.

Figure 6:
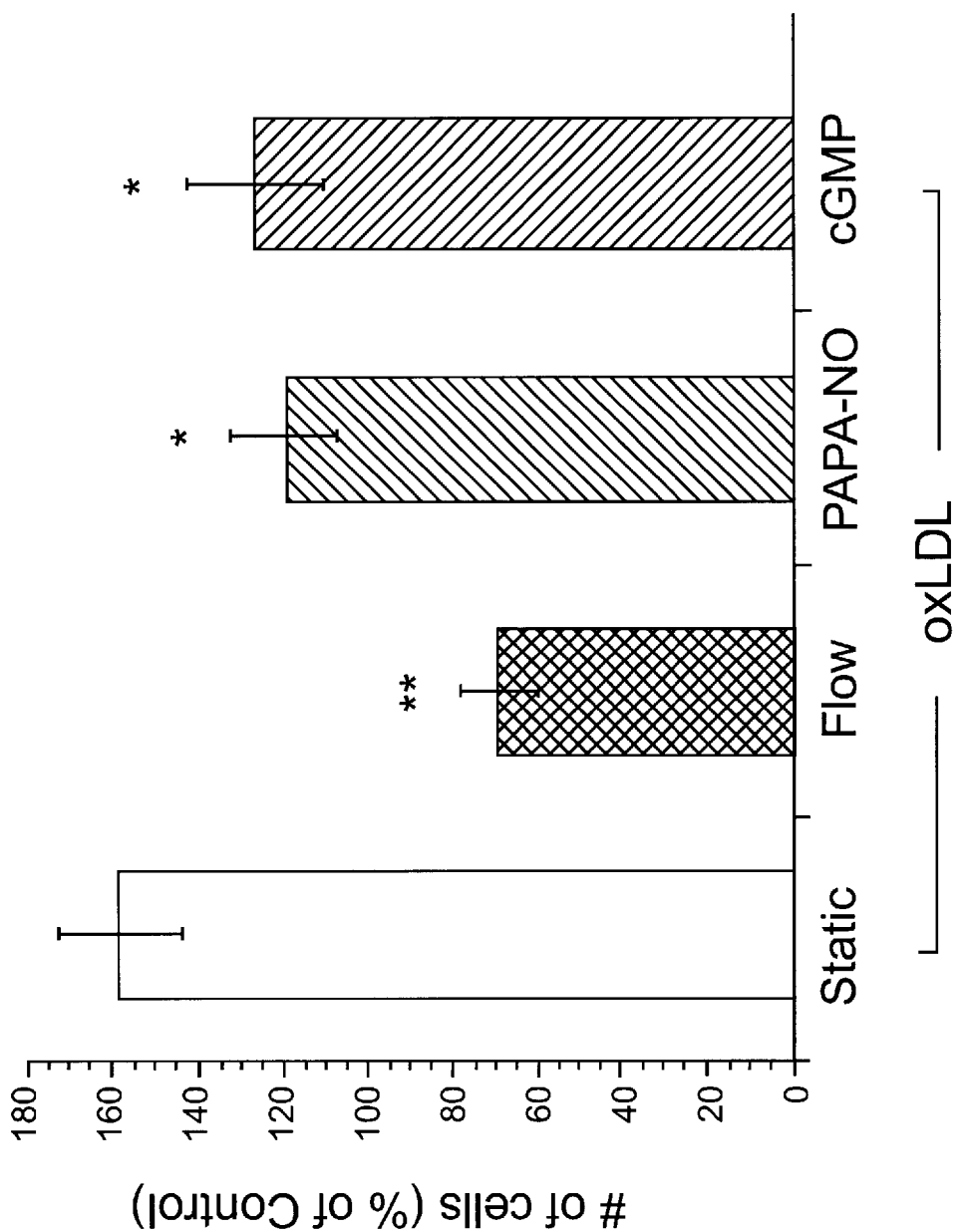
FIG. 6. Stimulation of cultured endothelial cells with fluid flow causes them to secrete nitric oxide. Flow-induced secretion of nitric oxide decreases endothelial adhesiveness induced by oxidized LDL cholesterol (oxLDL; 30 $\mu$g/ml). Exposure of human aortic endothelial cells to oxLDL increased the ex vivo binding of monocytes when compared to Control. In comparison to cells not exposed to flow (static), previous exposure to flow inhibited the monocyte adhesion induced by oxLDL. These effects of flow were blocked by NO synthase inhibitors and mimicked by NO donors (PAPA-NO) or cyclic GMP (cGMP). Bars represent mean±SEM. *$p<0.05$; **$p<0.01$. (See Ex. 8)

Methods and Results: Confluent monolayers of human aortic endothelial cells (HAEC) were exposed to static or fluid flow conditions for 4 hours (fluid flow stimulates the production of endogenous nitric oxide). Medium was then replaced and cells were then incubated with native LDL (50 µg/ml), oxidized LDL (30 µg/ml), or LPS (10 ng/ml)+ TNF-α (10 U/ml) for an additional 4 hours. Functional binding assays utilizing THP-1 monocytes were then performed. Superoxide production by HAECs was monitored by lucigenin chemiluminescence and expression of the adhesion molecules VCAM-1 and ICAM-1 was quantitated by flow cytometry. Whereas native LDL had little effect, incubation with either oxLDL or LPS/TNF significantly increased superoxide production, NF-κB activity, VCAM-1 expression and endothelial adhesiveness for monocytes. Previous exposure to fluid flow inhibited endothelial adhesiveness for monocytes (FIG. 6) and the other sequelae of exposure to cytokines or oxidized lipoprotein. The effect of fluid flow was due to shear-induced release of nitric oxide since coincubation with L-nitro-arginine completely abolished these effects of flow. Furthermore, the NO donor PAPA-NONOate mimicked the effects of flow.

Conclusions. Previous exposure to fluid flow decreased cytokine or lipoprotein-stimulated endothelial cell superoxide production, VCAM-1 expression and monocyte binding; the effects of flow are due at least in part to nitric oxide. NO participates in the regulation of the endothelial generation of superoxide anion and thereby inhibits oxidant-responsive transcription of genes (i.e. VCAM-1 and MCP-1) that are involved in atherogenesis.

EXAMPLE 9

Transfection of the Gene Encoding NO Synthase Increases NO Generation and Inhibits Monocyte Adherence The following experiment was done to determine if transfer of the gene encoding NO synthase (the enzyme that produces NO) could increase generation of nitric oxide and thereby inhibit monocyte adherence. Cultured endothelial cells (bEnd-3; a murine endothelial cell line) were transfected with a plasmid construct encoding the NO synthase gene, using lipofectamine liposomal technique. Forty-eight hours later, generation of nitric oxide was measured using chemiluminescence. Nitric oxide generation was increased 2-fold in cells transfected with the NO synthase construct (but not in cells transfected with a control construct). In parallel, binding assays were performed using a murine monocytoid cell line. The binding of monocytoid cells to the endothelial cells was reduced by 30% in those cells transfected with the NO synthase construct.

Conclusion: endothelial cells transfected with a plasmid construct containing the NO synthase gene were able to elaborate more nitric oxide. The increased elaboration of nitric oxide was associated with an inhibition of monocyte binding to the endothelial cells.

EXAMPLE 10

Effect of NO Synthase Expression on Proliferation of Vascular Smooth Muscle Cells Cultured rat aortic vascular smooth muscle cells under confluent quiescent conditions were studied. An efficient viral coat protein-mediated DNA transfer method was employed to transfect the cells with the NO synthase gene driven by the β-actin promoter and CMV enhancer. This resulted in increased NO synthase activity (as measured by the arginine-to-citrulline conversion assay) in comparison to control vector transfected cells. Transfection of the NO synthase gene completely abolished serum-stimulated DNA synthesis compared to control vector transfection. These results indicated that increased expression of NO synthase (associated with increased production of NO) inhibits excessive proliferation of vascular smooth muscle cells. This inhibition can be correlated with treatment of atherosclerosis and restenosis.

EXAMPLE 11

Gene Therapy Using NO Synthase CDNA Prevents Restenosis

The study above indicated that NO inhibits proliferation of vascular smooth muscle cells. In atherogenesis and restenosis, excessive proliferation of vascular smooth muscle cells contributes to lesion formation. Injury to the endothelium in atherosclerosis and after catheter interventions apparently reduces or removes the salutary influence of NO. The following study shows delivery of the gene for NO synthase to the vessel wall inhibits lesion formation.

A plasmid construct encoding the cDNA of endothelial-type NO synthase (EC-NOS) was synthesized. A full length cDNA encoding for EC-NOS was inserted into the EcoRI site of the pUCcaggs expression vector. Balloon angioplasties of the carotid artery in Sprague-Dawley rats were performed and HVJ-liposomes with plasmids encoding EC-NOS cDNA infused, or plasmids lacking EC-NOS cDNA (control vector) infused. After 4 days to 2 weeks, the rats were sacrificed and the carotid arteries harvested for: 1) histomorphometry; 2) measurement of DNA synthesis; and 3) ex vivo determination of NO synthesis and release by bioassay and by chemiluminescence.

Figure 7:
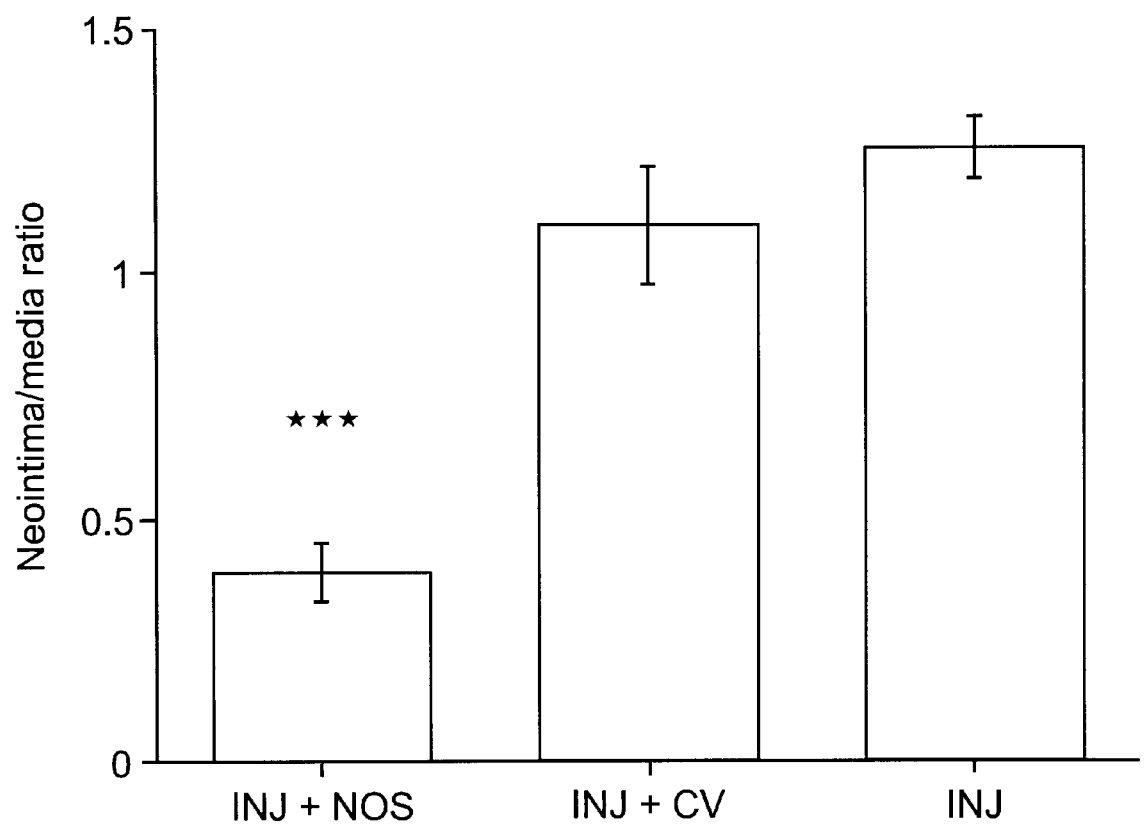
FIG. 7 is a bar diagram of morphometric measurements of intimal lesion thickening two weeks after a balloon angioplasty in animals treated with a plasmid construct containing the gene for NO synthase (INJ+NOS) in comparison to control vector (INJ+CV) or untreated injured vessels (INJ). (See Ex. 11)

Results. Morphometric measurements 2 weeks after injury revealed a significant (68%) reduction of intimal lesion thickness in EC-NOS treated (Inj+NOS) in comparison to control vector treated (Inj+CV) or untreated (Inj) injured vessels. (FIG. 7) Measurements of DNA synthesis were performed four days after injury using bromodeoxyuridine. EC-NOS transfection significantly limited bromodeoxyuridine incorporation (by 25%) in comparison to control vector treated or untreated injured vessels. Vessel segments were studied ex vivo using organ chamber technique to bioassay for NO release. Calcium ionophore increases intracellular calcium and activates NO synthase to produce NO. Calcium ionophore induced relaxations in injured carotid arteries transfected with control vector that were only 15% of uninjured vessels. Injured arteries that had been transfected with EC-NOS relaxed to a much greater degree, approximately 50% of that observed in uninjured vessels. Direct measurement of NO (by chemiluminescence) released into the medium revealed that NO released by injured tissues (transfected with the control vector) was only 20% of that released by normal uninjured tissues. By contrast, injured tissues transfected with EC-NOS released more NO (about 75% of normal).

To conclude, balloon angioplasty of the rat carotid artery removes the endothelial source of NO, induces excessive vascular smooth muscle DNA synthesis and proliferation, resulting in an intimal lesion (restenosis). Transfection of the vessel with EC-NOS at the time of balloon injury partially restores NO production by the vessel, and this is associated with reduced DNA synthesis and vascular smooth muscle proliferation, thereby reducing lesion formation. These results are consistent with the conclusion that NO is an endogenous antiatherogenic molecule.

EXAMPLE 12

Figure 8:
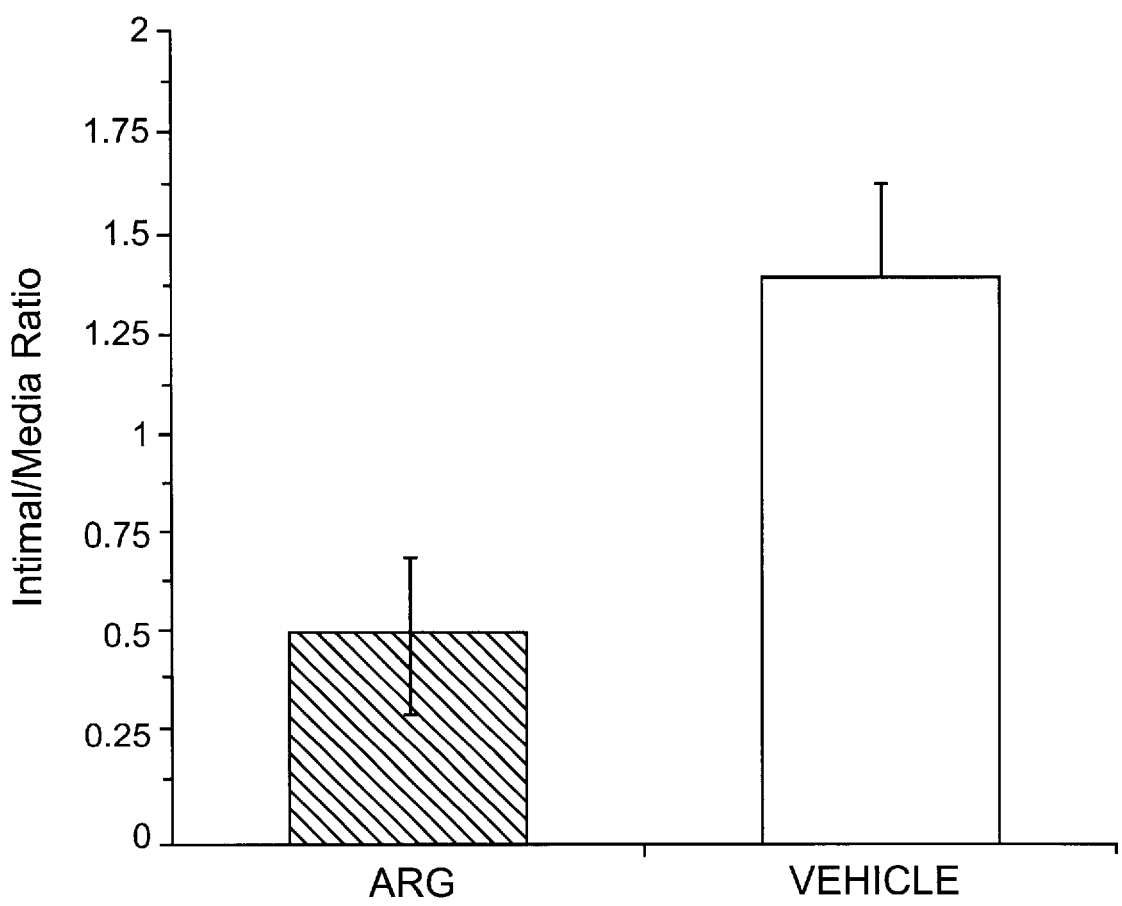
FIG. 8 is a histogram showing the effect of local intraluminal administration of arginine on restenosis. Hypercholesterolemic rabbits had balloon angioplasty of the iliac artery. Immediately thereafter some animals received an infusion of arginine directly into the vessel by means of a catheter designed to apply high local concentrations of arginine to the vessel. Two to four weeks later, vessels were removed from the animals, and examined microscopically. Thickening of the vessel wall (internal thickening or "restenosis") was reduced in the animals treated with intraluminal infusion of arginine (ARG) in comparison to those treated with vehicle. (See Ex. 12)

Local Application of L-arginine to the Vessel Wall Inhibits Myointimal Hyperplasia The previous studies revealed that oral administration of arginine could enhance vascular NO activity and inhibit lesion formation induced by a high cholesterol diet and/or vascular injury (with balloon angioplasty). To determine if intraluminal application of arginine to the vessel wall at the time of balloon angioplasty could inhibit lesion formation, the following study was performed. Rabbits (n=7) were fed a 1% cholesterol diet. After one week, angioplasty of the iliac arteries was performed. After angioplasty of one iliac artery, a local infusion catheter was used to expose the injured area to a high concentration of arginine (6 mM). The other iliac artery was subjected to balloon angioplasty, but not treated with a local infusion. After four weeks, the vessels were harvested, and segments of the arteries processed for histomorphometry. Initial thickening in the arginine-treated vessels was significantly reduced (FIG. 8). This study indicates that the local intraluminal application of high doses of arginine can reduce myointimal hyperplasia after vascular injury.

EXAMPLE 13

Exclusion of the Effect of Enhanced Nitrogen or Caloric Balance as Causing the Observed Results To exclude an effect of L-arginine on nitrogen or caloric balance as the cause of these results, six animals received 1% cholesterol diet supplemented by additional methionine to increase the dietary methionine six-fold. At ten weeks animals were sacrificed for studies of platelet and vascular reactivity, and histomorphometry. Endothelium-dependent relaxation, platelet aggregation and intimal thickness were not different from those of animals fed 1% cholesterol diet alone. These results reveal that another amino acid, methionine (which is not a precursor of NO) does not mimic the effect of the amino acid L-arginine. Therefore it seems likely that the effect of L-arginine is due to its metabolism to nitric oxide, rather than some other effect of amino acid administration (i.e. change in nitrogen or caloric balance).

EXAMPLE 14

L-lysine Enhances Vascular NO Activity and Inhibits Atherogenesis

Figure 9:
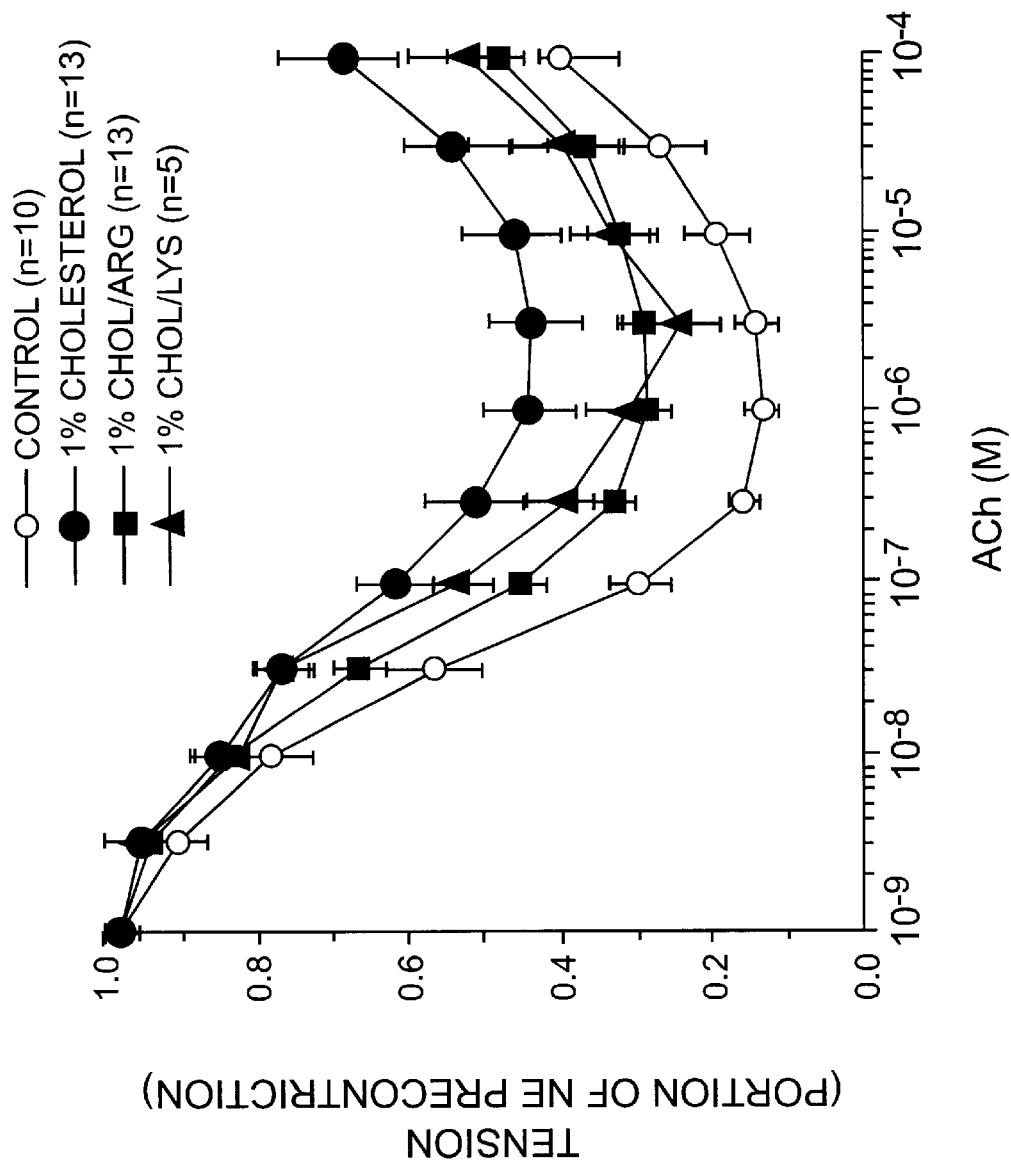
FIG. 9 is a set of dose-response curves showing the effect of chronic lysine administration on endothelium dependent vasodilation in hypercholesterolemic rabbits. Chronic oral administration of lysine (for ten weeks) improved NO-mediated vasodilation; this improvement in NO activity was also associated with a marked reduction in plaque area. Chronic administration of lysine was just as effective as arginine in restoring vascular function and structure. (See Ex. 14)

L-lysine is a basic amino acid like L-arginine, but is not known to be metabolized by NO synthase to NO. Therefore, the following results were unexpected. New Zealand white rabbits were fed a normal or high cholesterol chow (n=18). Half of the animals on the cholesterol diet also received oral L-lysine. After ten weeks, the thoracic aortae were harvested and bioassayed for. vascular NO synthesis, and histomorphometry to assess lesion formation was performed as described above. The administration of L-lysine was just as effective as L-arginine to increase vascular NO activity in the hypercholesterolemic animals as assessed by endothelium-dependent vasorelaxation. (FIG. 9) The improvement in vascular NO activity was associated with a marked reduction in vascular lesion formation.

This study revealed the unexpected result that L-lysine can enhance vascular NO activity and inhibit atherosclerosis.

EXAMPLE 15

Oral L-arginine Normalizes Monocyte Adhesiveness in Hypercholesterotemic Humans

Adherence of monocytes to the endothelium is the first observable event in the development of atherosclerosis. We hypothesized that chronic oral administration of L-arginine to hypercholesterolemic humans would enhance the generation of endothelium-derived NO, and thereby inhibit the interaction of monocytes with the endothelium. In this investigation we have developed a reproducible assay for the binding of human monocytes to cultured endothelial cells, and we have examined the effect of hypercholesterolemia and L-arginine treatment on this interaction.

The control subject population in this study included 12 normal volunteers, (10 males and 2 females), with an average age of 37±2 yrs. Normalcy was determined by a careful history, physical examination, and laboratory analysis to exclude individuals with hematologic, renal, or hepatic dysfunction or clinically evident atherosclerosis. There were 20 patients (10 males and 10 females) with hypercholesterolemia as defined by a total plasma cholesterol greater than 240 mg/dl and a LDL cholesterol level greater than 160 mg/dl. These individuals had an average age of 51±2 yrs . None of the subjects were taking diuretics, vasoactive medications, antiplatelet or hypolipidemic medications. This study was approved by the Stanford University Administrative Panel on Human Subjects in Medical Research and each subject gave written informed consent before entry into the study. Blood was drawn from each subject in the postabsorptive state.

We isolated human monocytes from citrated venous blood. The blood was centrifuged and the buffy coat removed and resuspended with HBSS. The suspension was then carefully layered onto a cushion of 1.068-d Histopaque, and centrifuged. After centrifugation, the monocytes were aspirated.

We used the transformed endothelial cell (EC) line, bEnd3 to examine monocyte-endothelial binding ex vivo. The bEnd3 cells express endothelial adhesion molecules and bind monocytes in a cytokine-inducible fashion with kinetics similar to those observed with human umbilical vein endothelium. Monocytes were added to the wells containing the endothelial monolayers to reach a final cell number of $3 \times 10^6$/ml. In some studies, monocytes were exposed in vitro for 30 minutes to sodium nitroprusside (an NO donor) prior to the binding assay.

The six-well plates were transferred to a rocking platform and rocked for 30 minutes at room temperature. After 30 minutes, the cell suspension was aspirated from each well and wells were then rinsed with binding buffer to remove non-adherent monocytes. Videomicroscopic counting of adherent cells was performed using a computer aided image analysis system.

Results. Oral administration of L-arginine (7 g daily for 2 weeks) to hypercholesterolemic humans increased plasma arginine values by 60% (from 79±10 to 128±12 mM; n=7), whereas L-arginine values in the placebo-treated (n=3) and normocholesterolemic (n=6) groups remained unchanged. The administration of oral L-arginine had no effect on any of the biochemical or hematologic parameters and was well tolerated. Oral L-arginine did not lower total cholesterol or LDL cholesterol. Two patients dropped out of the study; one because he did not want to take the pills, and one because of reactivation of oral herpes during the study.

Figure 10:
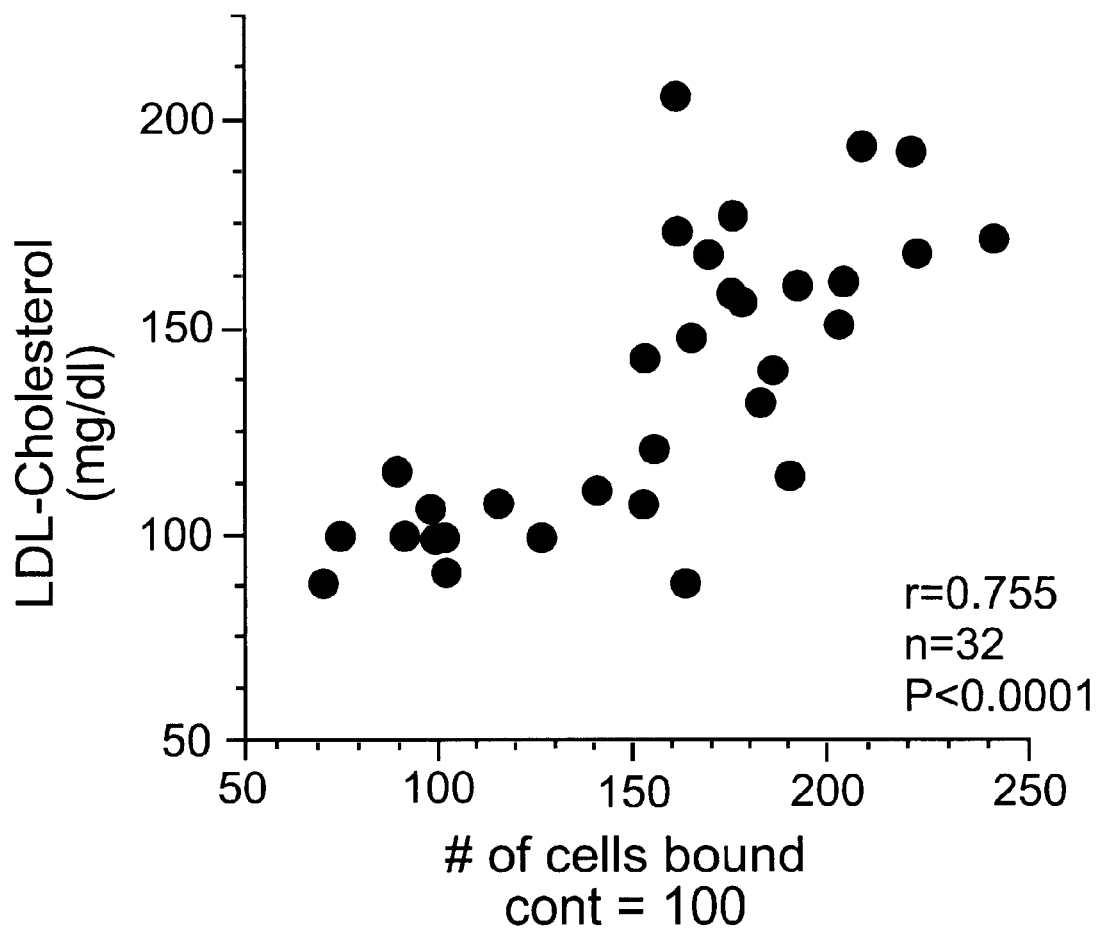
FIG. 10 is a scatter-diagram illustrating the relationship between the level of blood LDL-cholesterol and monocyte binding. Monocytes were isolated from the blood of humans with normal or elevated cholesterol levels. The binding of these monocytes to endothelial cells in culture was observed. Monocytes from individuals with high cholesterol levels have a greater adhesiveness for endothelial cells. This monocyte-endothelial cell interaction in vivo is the first step in the development of atherosclerotic plaque. (See Ex. 15)

The results of the adhesion assays were highly reproducible. Monocytes derived from hypercholesterolemic individuals demonstrated a 50±8% increase m bound cells/hpf in comparison to cells from normal individuals (p<0.0001). The degree of adhesiveness was correlated to the plasma levels of LDL cholesterol (R=0.7, n=33; p<0.0001; FIG. 10).

In an open-label study, 3 hypercholesterolemic individuals were treated with oral L-arginine supplementation for 2 weeks. Arginine treatment resulted in a 38% decrease in monocyte adhesiveness.

Figure 11:
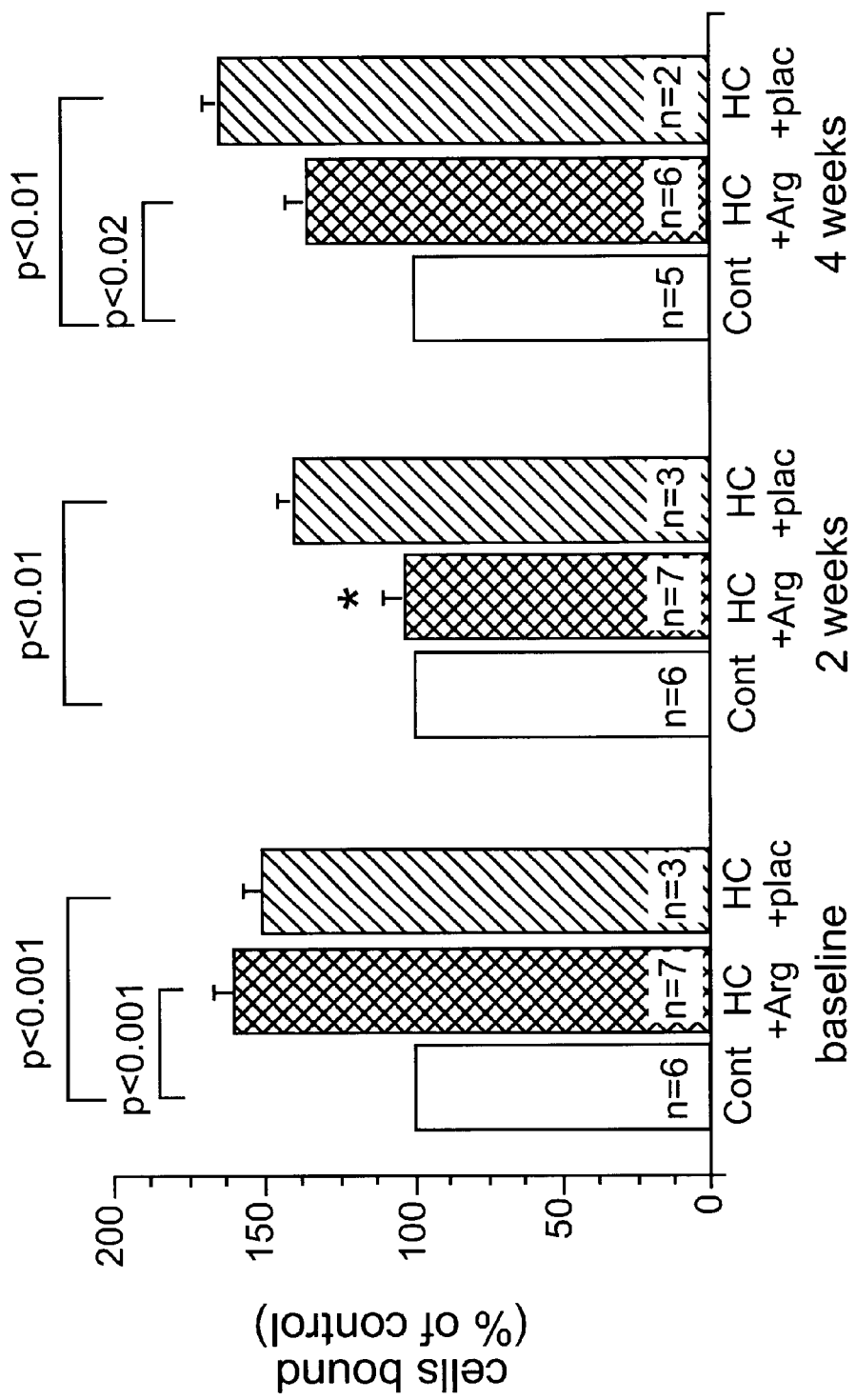
FIG. 11 is a bar diagram showing the adhesiveness of monocytes obtained from subjects with normal cholesterol levels (CONT) and those from hypercholesterolemic (HC) humans, before, during, and after treatment with arginine (the NO precursor). Prior to initiating arginine (Arg) or placebo (plac) treatment, monocytes from hypercholesterolemic individuals have a greater tendency to bind to endothelial cells ex vivo (baseline). After 2 weeks of arginine treatment monocytes from these hypercholesterolemic individuals have a significantly reduced adhesiveness and are no different from those of the normal subjects. At this point arginine therapy was discontinued and there was a washout (4 weeks). At this time point, monocytes from the patients previously treated with arginine now have increased adhesiveness, off of the arginine treatment. (See Ex. 15)

To confirm this effect of L-arginine treatment and to control for any experimental bias, a double-blinded, placebo-controlled, randomized study was performed. Ten hypercholesterolemic subjects were randomized (1:2) to placebo or L-arginine treatment; 6 normocholesterolemic individuals were studied in parallel to control for variation over time in the binding assay. At baseline, the adhesion of monocytes from both hypercholesterolemic groups was increased in comparison to the normocholesterolemic individuals (p<0.001). After 2 weeks of L-arginine administration, there was an absolute reduction of 53% in monocyte binding (n=7, p<0.005, baseline vs 2 weeks) (FIG. 11). By contrast, there was no significant change in the adhesiveness of monocytes isolated from hypercholesterolemic individuals treated with placebo. Two weeks after discontinuation of the L-arginine treatment, the adhesiveness of the monocytes isolated from hypercholesterolemic individuals had significantly increased compared to the normocholesterolemic individuals (34±9% increase in bound cells/hpf; p<0.05), and was also significantly increased in comparison to the binding obtained after 2 weeks of L-arginine therapy (an increase of 30±9%, p<0.05). The adhesiveness of monocytes from placebo-treated hypercholesterolemic individuals did not change significantly during the washout period.

Figure 12:
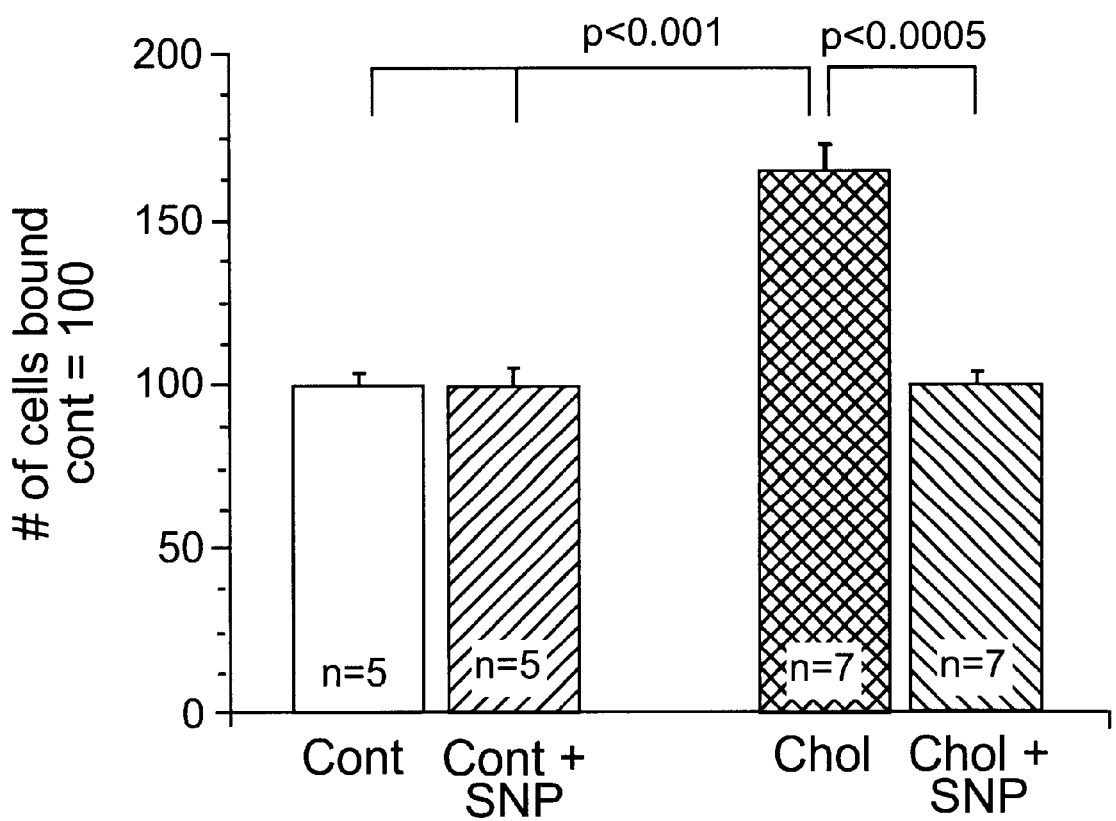
FIG. 12 is a bar diagram which shows that monocytes from individuals with elevated cholesterol (CHOL) have greater adhesiveness for endothelial cells. However, after treatment with sodium nitroprusside (CHOL+SNP), the adhesiveness of these monocytes is normalized. SNP is an NO donor. (See Ex. 15)

In some studies monocytes were exposed to sodium nitroprusside or vehicle control for 30 minutes in vitro. Pre-incubation of the cells from hypercholesterolemic individuals with the NO donor sodium nitroprusside ($10^{-5}$ M) markedly reduced binding (164±9% vs 98±7% vehicle vs sodium nitroprusside; n=7, p<0.0005; values expressed as a percent of the normocholesterolemic control exposed to vehicle; FIG. 12).

To conclude, the salient findings of this investigation are that: 1) Hypercholesterolemia enhances the adhesiveness of monocytes for endothelial cells, 2) oral arginine supplementation reverses the increase in adhesiveness of monocytes from hypercholesterolemic individuals, and 3) the effect of oral arginine is mimicked in vitro by exposure of the monocytes from hypercholesterolemic individuals to sodium nitroprusside, an NO donor.

EXAMPLE 16

Platelet Hyperaggregability in Hypercholesterolemic Humans: Reversal by Oral L-Arginine In this study we tested the hypothesis that chronic L-arginine supplementation would inhibit platelet reactivity in hypercholesterolemic humans. Venous blood was collected from normal (NC; n=11) and hypercholesterolemic (HC; n=22) volunteers for isolation of platelet-rich plasma and aggregometry. Half the HC group received L-arginine (7 g/d) for 2 weeks; aggregometry was performed using collagen (5 mg/ml) before and after two weeks of treatment.

Figure 13:
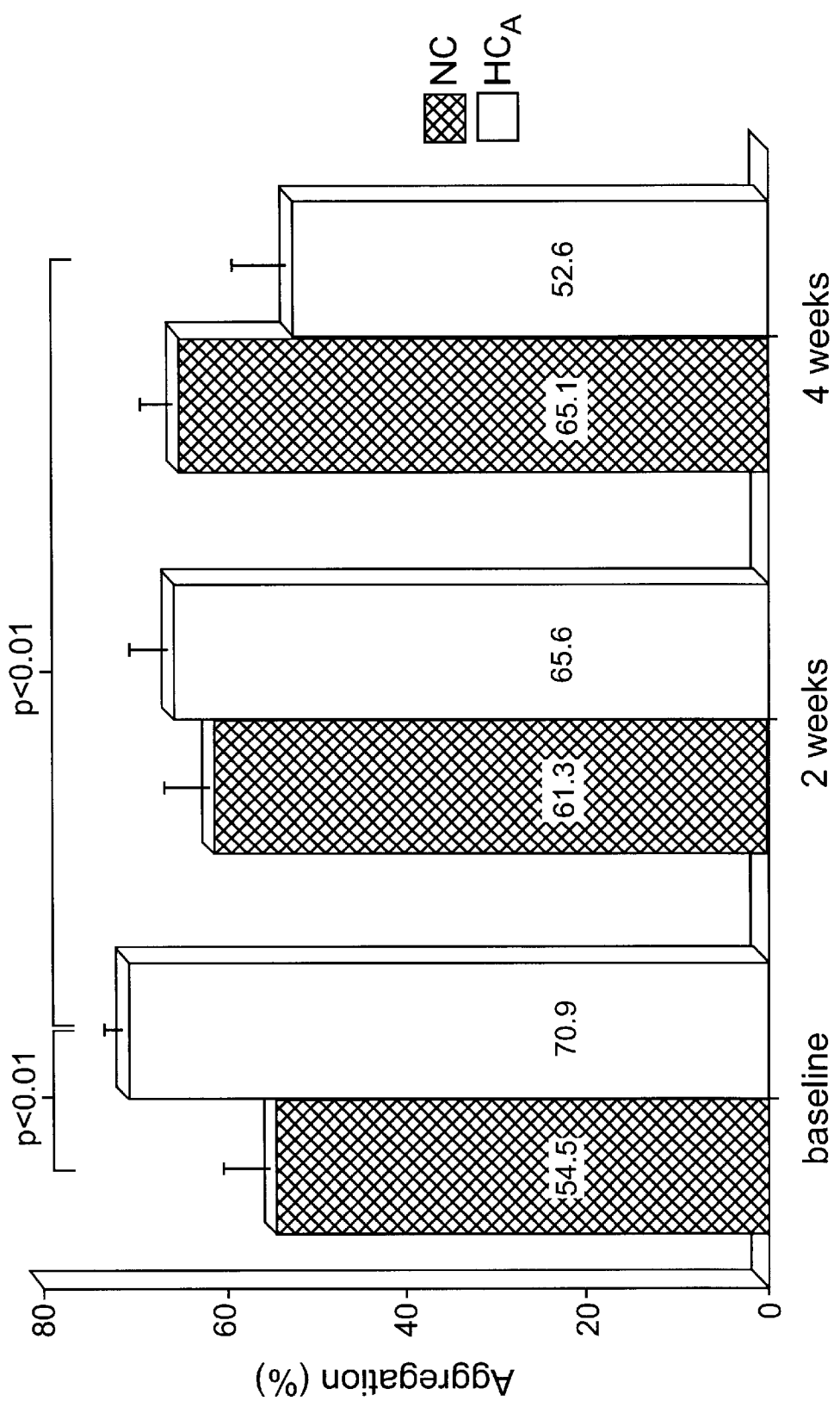
FIG. 13 is a set of histograms showing aggregation of platelets obtained in hypercholesterolemic humans (hc), and individuals with normal cholesterol levels (nc). Platelet aggregation ex vivo in response to adenosine diphosphate (ADP) is increased in hc individuals in comparison to normal individuals. After 2 weeks of treatment with oral L-arginine, platelet aggregation is attenuated in the hypercholesterolemic individuals, while an even greater effect of the treatment is seen at four weeks. (See Ex. 16)

Results: HC platelets were hyperaggregable. After two weeks of L-arginine, the aggregability of HC platelets was reduced (FIG. 13). These studies are consistent with our previous observations in animals that oral administration of L-arginine inhibits platelet reactivity.

EXAMPLE 17

Intravenous Administration of L-Arginine Improves Endothelium-dependent Vasodilation in Hypercholesterolemic Humans Hyperlipoproteinemia impairs endothelium-dependent vasodilation, even before the development of atherosclerosis. We hypothesized that administration of L-arginine may increase synthesis of NO and thereby improve endothelium-dependent vasodilation in hypercholesterolemia. Indeed, our earlier studies conducted in cholesterol-fed rabbits support this notion. The following data demonstrates that L-arginine augments endothelium-dependent vasodilation in forearm resistance vessels of hypercholesterolemic humans.

The control subject population in this study included 11 normal volunteers comprising (10 males and 1 female). Their ages ranged from 31 to 49 and averaged 39±2 yr. There were 14 patients with hypercholesterolemia. Hypercholesterolemia was defined as a serum LDL cholesterol level greater than the 75th percentile adjusted for age and sex. These individuals included 11 males and 3 females whose ages ranged from 22 to 48 and averaged 38±2 years.

Under local anesthesia and sterile conditions, a polyethylene catheter was inserted into a brachial artery of each subject for determination of blood pressure and for infusion of drugs. A separate polyethylene catheter was inserted into the antecubital vein for infusion of L-arginine. Bilateral forearm blood flow was determined by venous occlusion strain gauge plethysmography, using calibrated mercury-in-silastic strain gauges, and expressed as ml/100 ml tissue per min.

To assess NO-dependent vasodilation, methacholine chloride (which induces the endothelium to release NO) was administered via the brachial artery. Forearm blood flow was measured during infusion of methacholine chloride at concentrations of 0.3, 3, and 10 $\mu$g/min each for 3 min.

After completion of the methacholine chloride infusions, all normal subjects and 10 individuals with hypercholesterolemia were given L-arginine intravenously over 30 minutes and then the methacholine infusions were repeated. D-arginine, the enantiomer of L-arginine, is not a precursor of NO. Thus, to ensure that any observed effects of L-arginine were due to its contribution to the synthesis of NO and not just secondary to its physiochemical properties, five individuals with hypercholesterolemia received D-arginine intravenously.

Results. Baseline blood pressure, heart rate, and forearm blood flow did not differ between normal and hypercholesterolemic subjects. Intraarterial infusion of methacholine chloride caused a dose-dependent increase in forearm blood flow. In the hypercholesterolemic subjects, however, cholinergic vasodilation was less than that of normal subjects (p<0.05). The maximal forearm blood flow response to methacholine in normal subjects is 19.0±1.9 ml/100 ml of tissue per min, and in hypercholesterolemic subjects, it was 13.7±1.7 ml/100 ml of tissue per min (p<0.05).

In the normal subjects, L-arginine did not potentiate the vasodilation that occurred during the administration of methacholine chloride. In the hypercholesterolemic subjects, however, the L-arginine infusion augmented the vasodilation to methacholine chloride by 25% (p<0.05). There were no complications or side-effects of the L-arginine infusions.

The important findings in this study are: (a) endothelium-dependent vasodilation (due to the release of NO) is reduced in forearm resistance vessels of hypercholesterolemic humans; and (b) intravenous administration of L-arginine improves endothelium-dependent vasodilation in these individuals. NO not only causes vasodilation, but it also inhibits platelet aggregation and suppresses monocyte adhesion in hypercholesterolemic humans.

EXAMPLE 18

Administration of Intravenous L-Arginine Improves Coronary Endothelial Function in Cardiac Transplant Recipients A reduction in coronary NO-dependent vasodilation occurs in cardiac transplant recipients and may represent an early marker for the development of graft atherosclerosis. Reduced NO-dependent vasodilation in response to acetylcholine is an indicator of endothelial dysfunction and has been attributed to reduced synthesis or accelerated degradation of endothelium-derived nitric oxide. We hypothesized that endothelial dysfunction of epicardial coronary arteries at an early stage of coronary allograft atherosclerosis might be reversed by L-arginine. The present study tested the hypothesis that administration of L-arginine, the precursor of endothelium-derived NO, improves endothelial vasodilator function of coronary conduit and resistance vessels.

Cardiac transplant recipients scheduled for elective annual coronary angiography at Stanford University hospital were screened for possible participation in the study. The study protocol was approved by the Stanford University Committee on Human Subjects in Medical Research. All patients gave written informed consent. Eighteen patients who had cardiac transplantation 1 to 13 years previously were studied.

Vasoactive medications were discontinued at least 12 hours before the study. After diagnostic angiography revealed no visually apparent coronary stenosis, a guiding catheter was used to cannulate the left main coronary artery. An infusion catheter was then advanced over a Doppler flow velocity guide wire into a nonbranching segment of the coronary artery for infusion of acetylcholine (which stimulates the endothelium to release NO). After baseline angiography was performed, increasing concentrations of acetylcholine were serially infused over 3 minutes. Infusion of acetylcholine continued until the maximum dose ($10^{-4}$ mol/L) was reached or until total coronary occlusion occurred. Then an intravenous infusion of L-arginine (30 g over 15 minutes) was performed. Thereafter, the intracoronary infusion of acetylcholine was repeated. Coronary angiography and Doppler flow velocity recording was performed at the end of the L-arginine infusion and after the infusion of each concentration of acetylcholine.

Figure 14:
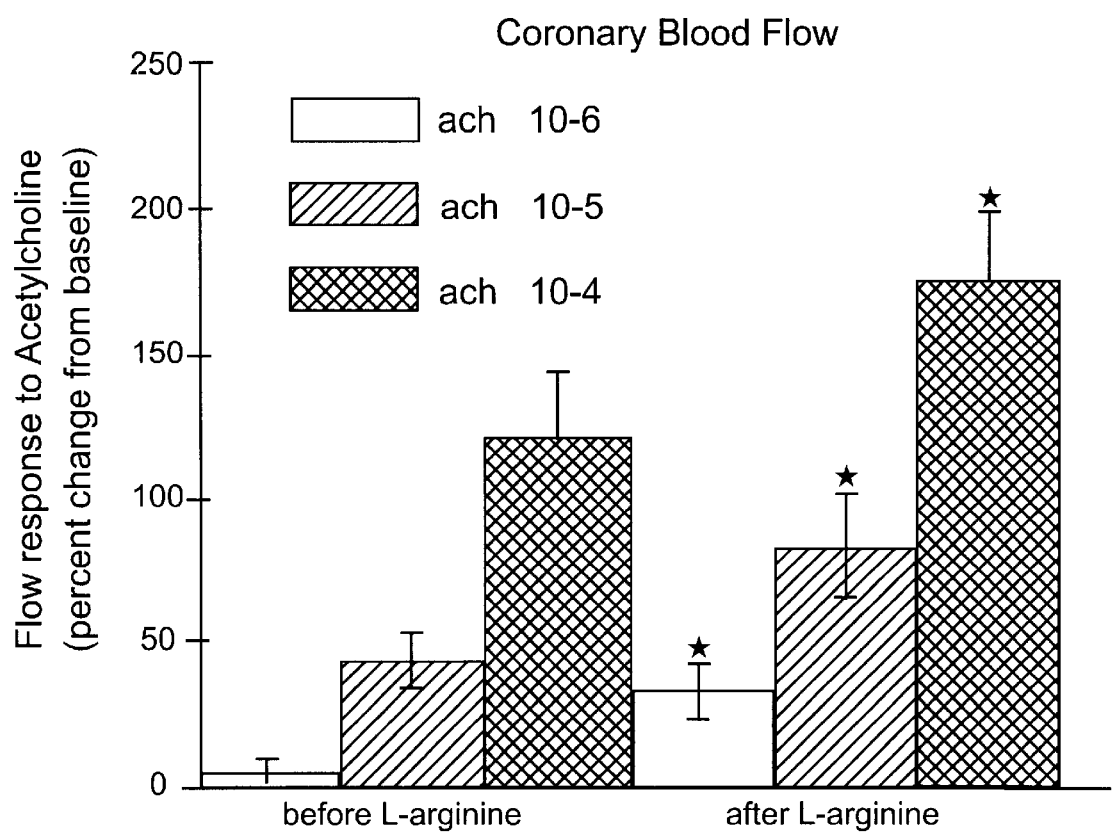
FIG. 14 is a bar graph showing increases in coronary blood flow in response to intracoronary infusions of acetylcholine (ACH) before and after intravenous infusion of L-arginine (30 g), in patients with transplant atherosclerosis. Acetylcholine stimulates the release of NO from the vessel wall causing vasodilation and increased blood flow. There is improved NO-dependent vasodilation after L-arginine administration. (See Ex. 18)

Results. In epicardial coronary arteries of these transplant recipients, acetylcholine caused vasoconstriction. Epicardial coronary vasoconstriction caused by acetylcholine was attenuated by infusion of L-arginine (10 mol/L, −6.8% versus −2.8%; p<.01). In coronary resistance vessels, acetylcholine induced vasodilation, reflected by increases in blood flow. The increase in coronary blood flow was significantly enhanced with L-arginine (p<.002; FIG. 14). There were no complications or side-effects of the L-arginine infusion.

The coronary vasculature of cardiac transplant recipients exhibits a generalized reduction of NO-dependent vasodilation. L-arginine improves endothelial-derived NO dependent vasodilation of both coronary microvasculature and epicardial coronary arteries.

It is evident from the above results, that by enhancing the nitric oxide levels, by means of nitric oxide precursor compounds or other compounds in the nitric oxide pathway, substantial benefits will ensue to patients with vascular degenerative diseases. This treatment will restore normal vascular tone (preventing excessive vasoconstriction and elevation of blood pressure; and will improve blood flow to the heart, brain, and other critical tissues thereby enhancing exercise tolerance and relieving symptoms such as angina or cerebral ischemia); and will diminish the formation of atherosclerotic plaque and restenosis (by inhibiting adhesion of monocytes and platelets, and by reducing the proliferation of vascular smooth muscle cells). Benefits may also ensue to normal individuals, because NO is critically involved in exercise-mediated vasodilation, an enhancement of NO synthesis could improve blood flow and exercise capacity even in normal individuals.

By virtue of administering to the host, based on a predetermined regimen, or providing in the host a supply of a component in the synthetic pathway for production of nitric oxide, so as to maintain a mildly elevated level of nitric oxide in the host, particularly at the site to be treated, the incidence of plaque formation can be substantially diminished. This can be achieved in a variety of ways: by oral administration in accordance with a predetermined regimen of various compounds associated with nitric oxide formation, e.g. L-arginine and/or L-lysine; by administration at the site, in a predetermined regimen of compounds which can produce nitric oxide, either directly or as a result of physiologic action of endogenous compounds, e.g. enzymes; by employing combinations of compounds, which by their action result in the production of nitric oxide; or the like. These individual administrations, can be done independently or in conjunction with a regimen of other compounds associated with the production of nitric oxide.

Alternatively, one may use genetic engineering to introduce a gene associated with a component in the synthetic pathway for production of nitric oxide, e.g. nitric oxide synthase, where the enhanced production of such compounds will have the effect of driving the equilibrium to an enhanced production of nitric oxide. Thus, the subject invention provides a plurality of pathways to enhance the synthesis or action of nitric oxide, or reduce the degradation of nitric oxide, thereby increasing the effect of endogenous nitric oxide to prevent the formation of vascular lesions and to inhibit restenosis.

All publications and patent applications cited in this specification are herein incorporated by reference as if each individual publication or patent application were specifically and individually indicated to be incorporated by reference.

Although the foregoing invention has been described in some detail by way of illustration and example for purposes of clarity of understanding, it will be readily apparent to those of ordinary skill in the art in light of the teachings of this invention that certain changes and modifications may be made thereto without departing from the spirit or scope of the appended claims.

What is claimed is:

1. A method of inhibiting adherence of leukocytes to vascular endothelial cells of a mammalian host, said method comprising:

administering a genetic construct comprising a gene encoding nitric oxide synthetase operably linked to a promoter to vascular endothelial cells at a site for leukocyte adherence, wherein said construct is administered intravascularly directly to said site and wherein said nitric oxide synthetase is expressed in vascular endothelial cells to enhance nitric oxide levels at said site and thereby inhibit said adherence of leukocytes at said site.

2. The method of claim 1, wherein said genetic construct is a plasmid.

3. The method of claim 1, wherein said leukocytes are monocytes.

4. The method of claim 1, wherein said site for leukocyte adherence is an injured vascular endothelium.

5. The method of claim 1, wherein said injured vascular endothelium is associated with a catheter intervention.

6. The method of claim 1, wherein said catheter intervention is a balloon angioplasty.

7. The method of claim 1, wherein said nitric oxide synthetase is an endothelial cell nitric oxide synthetase.

8. A method of improving NO-dependent vasodilation in a vasculature of a mammalian host, said method comprising:

administering a genetic construct comprising a gene encoding nitric oxide synthetase operably linked to a promoter to cells at a site for reduced NO-dependent vasodilation wherein said construct is administered intravascularly directly to said site and wherein said nitric oxide synthetase is expressed at said site to enhance the level of nitric oxide in the vasculature and improve NO-dependent vasodilation at said site.

9. The method of claim 8, wherein said genetic construct is a plasmid.

10. The method of claim 8, wherein said NO-dependent vasodilation is reduced as a consequence of disorders selected from the group consisting of: atherosclerosis, thrombosis, restenosis, congestive heart failure, Raynaud's phenomena, coronary vasospasm, cerebral vasospasm, hemolytic-uremia, impotence and cardiac or coronary transplant.

11. The method of claim 8, wherein said nitric oxide synthetase is an endothelial cell nitric oxide synthetase.

12. A method of inhibiting expression of a molecule involved in leukocyte accumulation on a vessel wall in a vascular system of a mammalian host, said method comprising:

administering a genetic construct expressing a nitric oxide synthetase operably linked to a promoter to cells of a vessel wall at a site for leukocyte accumulation, wherein said construct is administered intravascularly directly to said site and wherein expression of the nitric oxide synthetase enhances the level of nitric oxide at said site thereby inhibiting expression of a molecule involved in leukocyte accumulation at said site.

13. The method of claim 12, wherein said molecule involved in leukocyte accumulation is a chemokine.

14. The method of claim 13, wherein said chemokine is MCP-1.

15. The method of claim 12, wherein said molecule involved in leukocyte accumulation is an adhesion molecule.

16. The method of claim 15, wherein said adhesion molecule is selected from the group consisting of VCAM-1 and ICAM-1.

17. The method of claim 12, wherein said genetic construct is a plasmid.

18. The method of claim 12, wherein said administering is directly to a site for expression of the molecule involved in leukocyte accumulation.

19. The method of claim 18, wherein the site for expression of molecules involved in leukocyte accumulation is selected from the group consisting of: a vessel exposed to catheter intervention; a cardiac transplant and a coronary allotransplant.

20. The method of claim 19, wherein said catheter intervention is a balloon angioplasty.

21. The method of claim 12, wherein said nitric oxide synthetase is an endothelial cell nitric oxide synthetase.

* * * * *